(12) United States Patent
Tang et al.

(10) Patent No.: US 11,770,972 B2
(45) Date of Patent: Sep. 26, 2023

(54) MULTIFUNCTIONAL PHOTORESPONSIVE MATERIALS EXHIBITING AGGREGATION-INDUCED EMISSION AND SOLID-STATE ACTUATION

(71) Applicant: The Hong Kong University of Science and Technology, Hong Kong (CN)

(72) Inventors: Benzhong Tang, Hong Kong (CN); Haoran Wang, Hong Kong (CN); Hao Xing, Hong Kong (CN)

(73) Assignee: The Hong Kong University of Science and Technology, Hong Kong (CN)

(*) Notice: Subject to any disclaimer, the term of this patent is extended or adjusted under 35 U.S.C. 154(b) by 324 days.

(21) Appl. No.: 16/940,597

(22) Filed: Jul. 28, 2020

(65) Prior Publication Data

US 2021/0066615 A1 Mar. 4, 2021

Related U.S. Application Data

(60) Provisional application No. 62/922,835, filed on Sep. 3, 2019.

(51) Int. Cl.
  *C07D 263/57* (2006.01)
  *H10K 85/60* (2023.01)
  *C09K 11/06* (2006.01)
  *B81B 3/00* (2006.01)

(52) U.S. Cl.
  CPC ......... *H10K 85/657* (2023.02); *B81B 3/0029* (2013.01); *C07D 263/57* (2013.01); *C09K 11/06* (2013.01); *B81B 2201/032* (2013.01); *C09K 2211/1007* (2013.01); *C09K 2211/1018* (2013.01)

(58) Field of Classification Search
  CPC .................................................. C07D 263/57
  See application file for complete search history.

(56) References Cited

PUBLICATIONS

W. Zhang et al., 19 Chinese Journal of Chemistry, 695-701 (2001) (Year: 2001).*
I. Ishikawa et al., 99 Synthesis, 198-205 (2006) (Year: 2006).*
F. Li et al., 20 Chemistry of Materials, 1194-1196 (2008) (Year: 2008).*
Zhang et al.; Structure and Photochemical Properties of r-1, c-2, t-3, t-4-1,3-Bis[2-(5-R-benzoxazolyl)]-2,4-di(4-R'-phenyl) cyclobutane; Chinese Journal of Chemistry; 2001; vol. 19, No. 7; pp. 695-701.
Wang et al.; Bending, Curling, Rolling, and Salient Behavior of Molecular Crystals Driven by [2+2] Cycloaddition of a Styrylbenzoxazole Derivative; Angewandte Chemie International Edition; 2017; vol. 56; pp. 9463-9467.
Li et al.; A Rewritable Optical Data Storage Material System by [2+2] Photocycloreversion-Photocycloaddition; Chemistry of Materials; 2008; vol. 20; pp. 1194-1196.
Meher et al.; Functional group engineering in naphthalimides: a conceptual insight to fine-tune the supramolecular self-assembly and condensed state luminescence; Nanoscale; 2019; vol. 11; pp. 13233-13242.
Feng-Yu Li et. al., "c-2,t-4-Bis(2-benzoxazol-2-yl)-r-1,t-3-bis[4-(dimethylamino)phenyl]cyclobutane", Acta Cryst., 2007, E63, 20170705o1171-o1172.

* cited by examiner

*Primary Examiner* — Alexander R Pagano
(74) *Attorney, Agent, or Firm* — S&F/WEHRW

(57) ABSTRACT

Provided herein are multifunctional photoresponsive compositions that can undergo conversion from an aggregation-caused quenching (ACQ) state to an aggregation-induced emission (AIE) state and macroscopic actuation and systems comprising the same and methods of use thereof.

4 Claims, 23 Drawing Sheets

MULTIFUNCTIONAL PHOTORESPONSIVE MATERIALS EXHIBITING AGGREGATION-INDUCED EMISSION AND SOLID-STATE ACTUATION

CROSS-REFERENCE TO RELATED APPLICATIONS

This application claims the benefit of priority of U.S. Provisional Application No. 62/922,835, filed on Sep. 3, 2019, the contents of which being hereby incorporated by reference in their entirety for all purposes.

TECHNICAL FIELD

The present disclosure relates to multifunctional photoresponsive compositions exhibiting aggregation-induced emission (AIE) and solid-state actuation in response to optical stimulation, systems comprising the same and methods of use thereof.

BACKGROUND

The quest for efficient luminescent materials that can keep their function in solid state has recently been brought into the focus of photo and solid-state chemistry, due to their significant roles in technological innovation and practical implications. In most cases, chromophores that show high fluorescence quantum yields in dilute solutions become nonfluorescent in aggregation and solid state, where intermolecular interactions often cause self-quenching. This effect, sometimes referred to as aggregation-caused quenching (ACQ), poses significant difficulties for the development of solid-state fluorescence devices, such as organic light-emitting diodes and luminescence-based sensors. Some chromophores, however, display the opposite effect: they show no emission in dilute solution but are highly emissive upon concentration or solidification. This recently discovered phenomenon of aggregation-induced emission (AIE) is key for overcoming the ACQ effect and obtaining highly efficient light-emitting solid materials.

Inspired by this, scientists have spent many years tinkering with ACQ molecules, in order to convert normal ACQ chromophores to AIE luminogens upon introducing known AIE groups or aromatic rotors to the periphery of the planar π structure. However, most of the reported methods focused on structural modification, which undoubtedly requires tedious synthesis with unavoidable byproducts. To date, finding a simple and atom economical approach to obtaining solid-state light-emitting materials remains a major challenge.

Another area of interest is the development of systems that exhibit on-demand photoswitching with multiple functionalities. Most systems reported to date possess only one specific function. For example, U.S. Pat. No. 8,648,206 teaches actuator elements comprising a relatively complex tetra-substituted dithiazoleethene compound that changes shape upon exposure to light, but the luminescent properties of the system are not reported. Moreover, the dithiazoleethene compounds require a multistep synthesis to prepare.

There thus exists a need to develop easily prepared optically driven materials and systems that exhibit multiple functionalities, such as macroscopic actuation and/or AIE.

SUMMARY

Provided herein are solid-state materials that are capable of undergoing photodriven [2+2] cycloaddition that results in an ACQ-to-AIE transformation and substantial macroscopic actuation due to a large change in volume of the cycloadduct.

In a first aspect, provided herein is a method for conversion of a first compound exhibiting aggregation-caused quenching (ACQ) to a second compound exhibiting aggregation-induced emission (AIE), the method comprising: providing a crystal comprising the first compound, wherein the first compound is a compound of Formula 1:

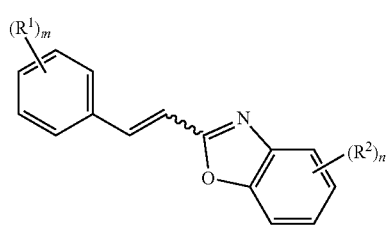

or a conjugate salt thereof, wherein each of m and n are independently a whole number selected from 0-4; and each of $R^1$ and $R^2$ is independently hydrogen, halide, nitrile, nitro, OR, $N(R)_2$, $O(C=O)R$, $N(R)(C=O)R$, $(C=O)R$, $CO_2R$, CHO, $(C=O)NR(R)_2$, $N(R)(C=O)NR(R)_2$, $O(C=O)NR(R)_2$, $N(R)(C=O)OR$, $-SO_2R$, $-SO_2NR_2$, alkyl, cycloalkyl, alkenyl, alkynyl, aryl, heterocycloalkyl, heteroaryl, or $-(CR_2)_pA$, wherein R for each occurrence is independently alkyl, cycloalkyl, alkenyl, alkynyl, aryl, heterocycloalkyl, or heteroaryl; or two instance of R taken together form a 5-6 membered heterocycloalkyl; p for each occurrence is independently a whole number selected from 0-20; and A is $-CO_2H$, $-C\equiv CH$, $-CNS$, $-N_3$, $-NH_2$, $-SH$, Cl, Br, I, or N-maleimide; or two instance of $R^1$ taken together form a 5-6 membered cycloalkyl, heterocycloalkyl, aryl, or heteroaryl; or two instance of $R^2$ taken together form a 5-6 membered cycloalkyl, heterocycloalkyl, aryl, or heteroaryl; and photoirradiating the compound of Formula 1 with ultraviolet (UV) light causing it to undergo photodimerization by [2+2] cycloaddition thereby forming the second compound, wherein the second compound is at least one of a compound of Formula 2a or a compound of Formula 2b:

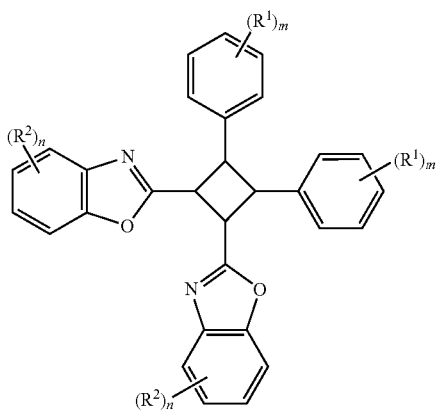

-continued

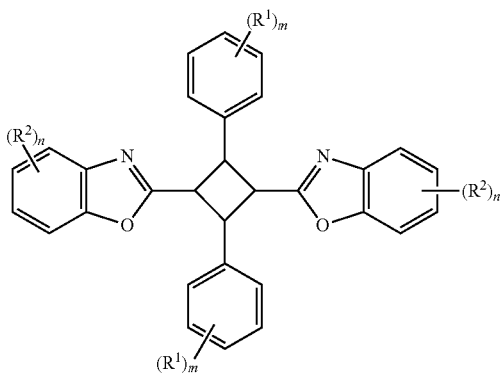

2b wherein photodimerization of the first compound optionally causes macroscopic actuation of the crystal.

In a first embodiment of the first aspect, provided herein is the method of the first aspect, wherein m and n are independently 0 or 1; and $R^1$ and $R^2$ is independently hydrogen, halide, nitrile, nitro, OR, $N(R)_2$, $O(C=O)R$, $N(R)(C=O)R$, $(C=O)R$, $CO_2R$, CHO, $(C=O)NR(R)_2$, $N(R)(C=O)NR(R)_2$, $O(C=O)NR(R)_2$, $N(R)(C=O)OR$, $-SO_2R$, $-SO_2NR_2$, alkyl, cycloalkyl, alkenyl, alkynyl, aryl, heterocycloalkyl, heteroaryl, or $-(CR_2)_pA$.

In a second embodiment of the first aspect, provided herein is the method of the first aspect, wherein m and n are independently 0 or 1; and each of $R^1$ and $R^2$ is independently hydrogen, halide, alkyl, cycloalkyl, alkenyl, alkynyl, aryl, heterocycloalkyl, or heteroaryl.

In a third embodiment of the first aspect, provided herein is the method of the first aspect, wherein the first compound has Formula 1a:

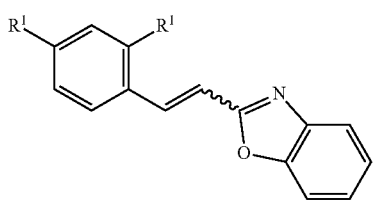

1a wherein $R^1$ for each instance is independently hydrogen, halide, nitrile, nitro, OR, $N(R)_2$, $O(C=O)R$, $N(R)(C=O)R$, $(C=O)R$, $CO_2R$, CHO, $(C=O)NR(R)_2$, $N(R)(C=O)NR(R)_2$, $O(C=O)NR(R)_2$, $N(R)(C=O)OR$, $-SO_2R$, $-SO_2NR_2$, alkyl, cycloalkyl, alkenyl, alkynyl, aryl, heterocycloalkyl, heteroaryl, or $-(CR_2)_pA$, wherein R for each occurrence is independently alkyl, cycloalkyl, alkenyl, alkynyl, aryl, heterocycloalkyl, or heteroaryl.

In a fourth embodiment of the first aspect, provided herein is the method of the first aspect, wherein the first compound is selected from the group consisting of:

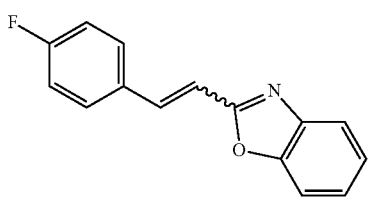

-continued

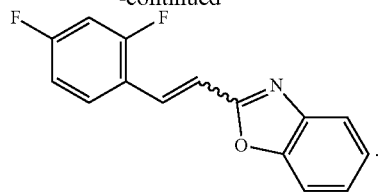

and

In a second aspect, provided herein is a photoresponsive actuation system, the system comprising: a UV light source; and a photoresponsive actuator element comprising a crystal, wherein the crystal comprises a first compound, wherein the first compound is a compound of Formula 3:

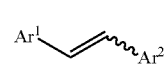

3 or a conjugate salt thereof, wherein each of $Ar^1$ and $Ar^2$ are independently aryl or heteroaryl, wherein photoirradiating the first compound with UV light from the UV light source causes the compound of Formula 3 to undergo photodimerization by [2+2] cycloaddition thereby forming a second compound, wherein the second compound is at least one of a compound of Formula 4a and a compound of Formula 4b:

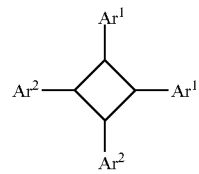

4a

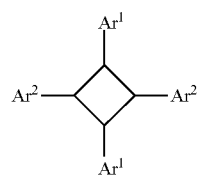

4b wherein photodimerization of the first compound causes actuation of the photoresponsive actuator element.

In a first embodiment of the second aspect, provided herein is the system of the second aspect, wherein $Ar^1$ is optionally substituted phenyl and $Ar^2$ is optionally substituted 2-benzoxazolyl.

In a second embodiment of the second aspect, provided herein is the system of the second aspect, wherein the first compound has Formula 1:

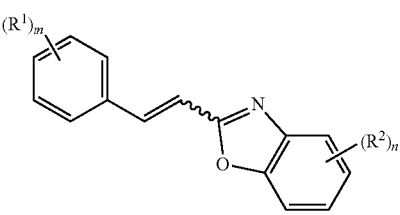

1 m and n are independently a whole number selected from 0-4; and each of $R^1$ and $R^2$ is independently hydrogen, halide, nitrile, nitro, OR, $N(R)_2$, O(C=O)R, N(R)(C=O)R, (C=O)R, $CO_2R$, CHO, (C=O)NR$(R)_2$, N(R)(C=O)NR$(R)_2$, O(C=O)NR$(R)_2$, N(R)(C=O)OR, —SO$_2$R, —SO$_2$NR$_2$, alkyl, cycloalkyl, alkenyl, alkynyl, aryl, heterocycloalkyl, heteroaryl, or —(CR$_2$)$_p$A, wherein R for each occurrence is independently alkyl, cycloalkyl, alkenyl, alkynyl, aryl, heterocycloalkyl, or heteroaryl; or two instance of R taken together form a 5-6 membered heterocycloalkyl; p for each occurrence is independently a whole number selected from 0-20; and A is —CO$_2$H, —C≡CH, —CNS, —N$_3$, —NH$_2$, —SH, Cl, Br, I, or N-maleimide; or two instance of $R^1$ taken together form a 5-6 membered cycloalkyl, heterocycloalkyl, aryl, or heteroaryl; or two instance of $R^2$ taken together form a 5-6 membered cycloalkyl, heterocycloalkyl, aryl, or heteroaryl.

In a third embodiment of the second aspect, provided herein is the system of second embodiment of the second aspect, wherein m and n are independently 0 or 1; and $R^1$ and $R^2$ is independently hydrogen, halide, nitrile, nitro, OR, $N(R)_2$, O(C=O)R, N(R)(C=O)R, (C=O)R, $CO_2R$, CHO, (C=O)NR$(R)_2$, N(R)(C=O)NR$(R)_2$, O(C=O)NR$(R)_2$, N(R)(C=O)OR, —SO$_2$R, —SO$_2$NR$_2$, alkyl, cycloalkyl, alkenyl, alkynyl, aryl, heterocycloalkyl, heteroaryl, or —(CR$_2$)$_p$A.

In a fourth embodiment of the second aspect, provided herein is the system of second embodiment of the second aspect, wherein m and n are independently 0 or 1; and each of $R^1$ and $R^2$ is independently hydrogen, halide, alkyl, cycloalkyl, alkenyl, alkynyl, aryl, heterocycloalkyl, or heteroaryl.

In a fifth embodiment of the second aspect, provided herein is the system of the second aspect, wherein the first compound has Formula 1a:

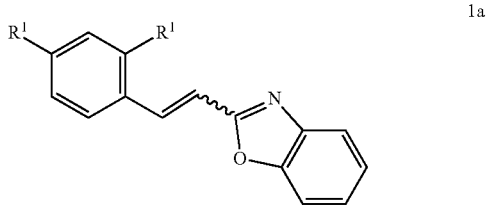

1a wherein $R^1$ for each instance is independently hydrogen, halide, nitrile, nitro, OR, $N(R)_2$, O(C=O)R, N(R)(C=O)R, (C=O)R, $CO_2R$, CHO, (C=O)NR$(R)_2$, N(R)(C=O)NR$(R)_2$, O(C=O)NR$(R)_2$, N(R)(C=O)OR, —SO$_2$R, —SO$_2$NR$_2$, alkyl, cycloalkyl, alkenyl, alkynyl, aryl, heterocycloalkyl, heteroaryl, or —(CR$_2$)$_p$A, wherein R for each occurrence is independently alkyl, cycloalkyl, alkenyl, alkynyl, aryl, heterocycloalkyl, or heteroaryl.

In a sixth embodiment of the second aspect, provided herein is the system of the second aspect, wherein the first compound is selected from the group consisting of:

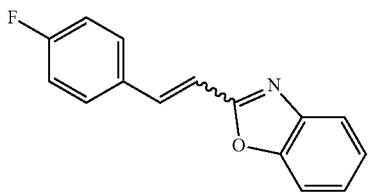

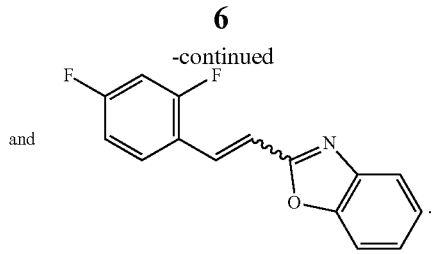

-continued and

In a seventh embodiment of the second aspect, provided herein is the system of the second aspect, wherein the photoresponsive actuator element is present a thin layer on the surface of a substrate.

In a third aspect, provided herein is a method for operating the photoresponsive actuator system of the second aspect, the method comprising: providing the photoresponsive actuator element; and photoirradiating the first compound with ultraviolet light from the UV light source thereby causing actuation of the photoresponsive actuator element.

In a first embodiment of the third aspect, provided herein is the method of the third aspect, wherein AO is optionally substituted phenyl and Are is optionally substituted 2-benzoxazolyl.

In a second embodiment of the third aspect, provided herein is the method of the third aspect, wherein the first compound has Formula 1:

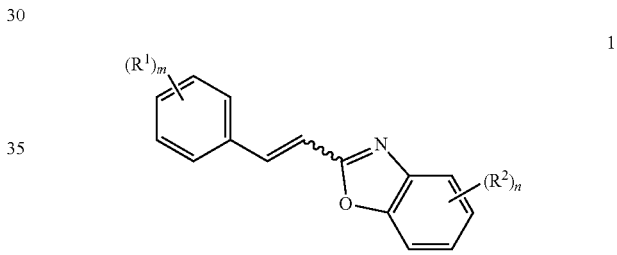

1 m and n are independently a whole number selected from 0-4; and each of $R^1$ and $R^2$ is independently hydrogen, halide, nitrile, nitro, OR, $N(R)_2$, O(C=O)R, N(R)(C=O)R, (C=O)R, $CO_2R$, CHO, (C=O)NR$(R)_2$, N(R)(C=O)NR$(R)_2$, O(C=O)NR$(R)_2$, N(R)(C=O)OR, —SO$_2$R, —SO$_2$NR$_2$, alkyl, cycloalkyl, alkenyl, alkynyl, aryl, heterocycloalkyl, heteroaryl, or —(CR$_2$)$_p$A, wherein R for each occurrence is independently alkyl, cycloalkyl, alkenyl, alkynyl, aryl, heterocycloalkyl, or heteroaryl; or two instance of R taken together form a 5-6 membered heterocycloalkyl; p for each occurrence is independently a whole number selected from 0-20; and A is —CO$_2$H, —C≡CH, —CNS, —N$_3$, —NH$_2$, —SH, Cl, Br, I, or N-maleimide; or two instance of $R^1$ taken together form a 5-6 membered cycloalkyl, heterocycloalkyl, aryl, or heteroaryl; or two instance of $R^2$ taken together form a 5-6 membered cycloalkyl, heterocycloalkyl, aryl, or heteroaryl.

In a third embodiment of the third aspect, provided herein is the method of the second embodiment of the third aspect, wherein m and n are independently 0 or 1; and $R^1$ and $R^2$ is independently hydrogen, halide, nitrile, nitro, OR, $N(R)_2$, O(C=O)R, N(R)(C=O)R, (C=O)R, $CO_2R$, CHO, (C=O)NR$(R)_2$, N(R)(C=O)NR$(R)_2$, O(C=O)NR$(R)_2$, N(R)(C=O)OR, —SO$_2$R, —SO$_2$NR$_2$, alkyl, cycloalkyl, alkenyl, alkynyl, aryl, heterocycloalkyl, heteroaryl, or —(CR$_2$)$_p$A.

In a fourth embodiment of the third aspect, provided herein is the method of the second embodiment of the third aspect, wherein m and n are independently 0 or 1; and each of $R^1$ and $R^2$ is independently hydrogen, halide, alkyl, cycloalkyl, alkenyl, alkynyl, aryl, heterocycloalkyl, or heteroaryl.

In a fifth embodiment of the third aspect, provided herein is the method of the third aspect, wherein the first compound has Formula 1a:

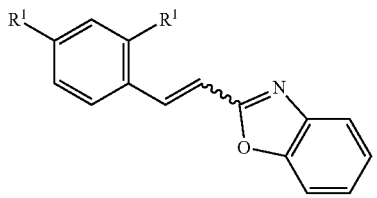

1a wherein $R^1$ for each instance is independently hydrogen, halide, nitrile, nitro, OR, $N(R)_2$, O(C=O)R, N(R)(C=O)R, (C=O)R, $CO_2R$, CHO, (C=O)NR$(R)_2$, N(R)(C=O)NR $(R)_2$, O(C=O)NR$(R)_2$, N(R)(C=O)OR, —SO$_2$R, —SO$_2$NR$_2$, alkyl, cycloalkyl, alkenyl, alkynyl, aryl, heterocycloalkyl, heteroaryl, or —(CR$_2$)$_p$A, wherein R for each occurrence is independently alkyl, cycloalkyl, alkenyl, alkynyl, aryl, heterocycloalkyl, or heteroaryl.

In a sixth embodiment of the third aspect, provided herein is the method of the third aspect, wherein the first compound is selected from the group consisting of:

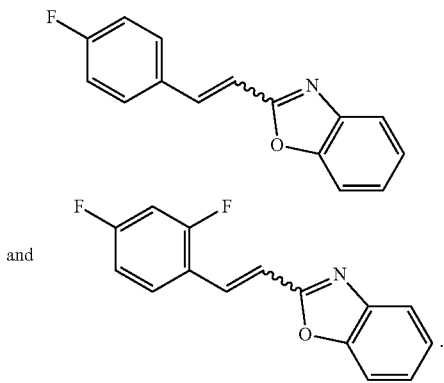

and

.

Disclosed herein is a novel class of AIE luminogens with "living" emissive and actuation properties. t-FSBO and t-2FSBO are typical ACQ molecules that do not exhibit emissions in the solid state due to extensive π-π interactions. After UV irradiation, photo-induced [2+2] cycloaddition occurs, and the resulting products t-FPCBO, t-2FPCBO, and c-2FPCBO become AIE-active. Intramolecular or intermolecular through-space conjugation is confirmed to be the key factor for the luminescence of these non-conjugated molecules. This novel in-situ ACQ-to-AIE transformation is thus a general approach to obtain solid-state light-emitting materials with simplicity and atom economics. More interestingly, t-FSBO crystals respond mechanically to photoexcitation, exhibiting the so-called photosalient effect. By coating t-FSBO on nitrile butadiene rubber glove, macroscopic mechanical motion was achieved, by amplifying the collective molecular motion from nanoscale up to macroscopic dimensions. The approach we described here should be helpful to enlighten the use of numerous already invented solid-state emitters and facilitate design of "living" luminogens with more rational strategies.

BRIEF DESCRIPTION OF DRAWINGS

The above and other objects and features of the present disclosure will become apparent from the following description of the disclosure, when taken in conjunction with the accompanying drawings.

DETAILS DESCRIPTION

Definitions

Figure 1:
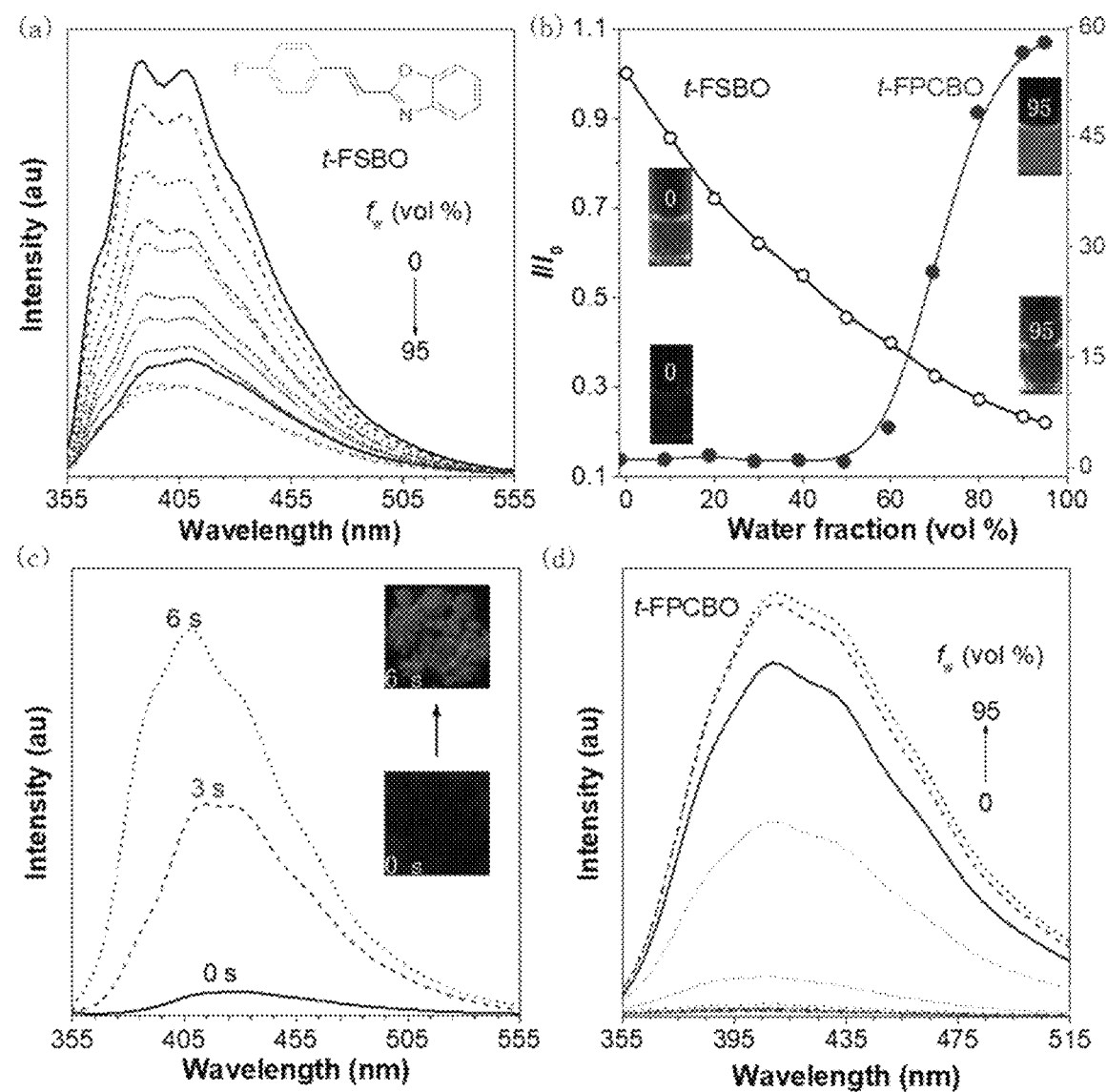
FIG. 1 shows (a) PL spectra of t-FSBO in DMSO/water mixture with different water fractions ($f_w$). (b) Plots of relative $\alpha_{AIE}$ value versus $f_w$ of t-FSBO at 392 nm and t-FPCBO at 411 nm. $c=5\times10^{-4}$ M, $\lambda_{ex}=330$ nm. Inset: fluorescent photos of t-FSBO and t-FPCBO in DMSO/water mixture with 0% and 95% water fractions taken under 365 nm UV light irradiation. (c) fluorescence emission ($\lambda_{ex}=330$ nm) spectra of t-FSBO microcrystals before and after irradiated by 365 nm light for different times. Inset: photos of t-FSBO microcrystals under UV light for 0 s and 6 s. (d) PL spectra of t-FPCBO in DMSO/water mixture with different water fractions ($f_w$), $\lambda_{ex}=320$ nm. (e) Chemical and single crystal structures of t-FSBO and t-FPCBO.
Figure 1:
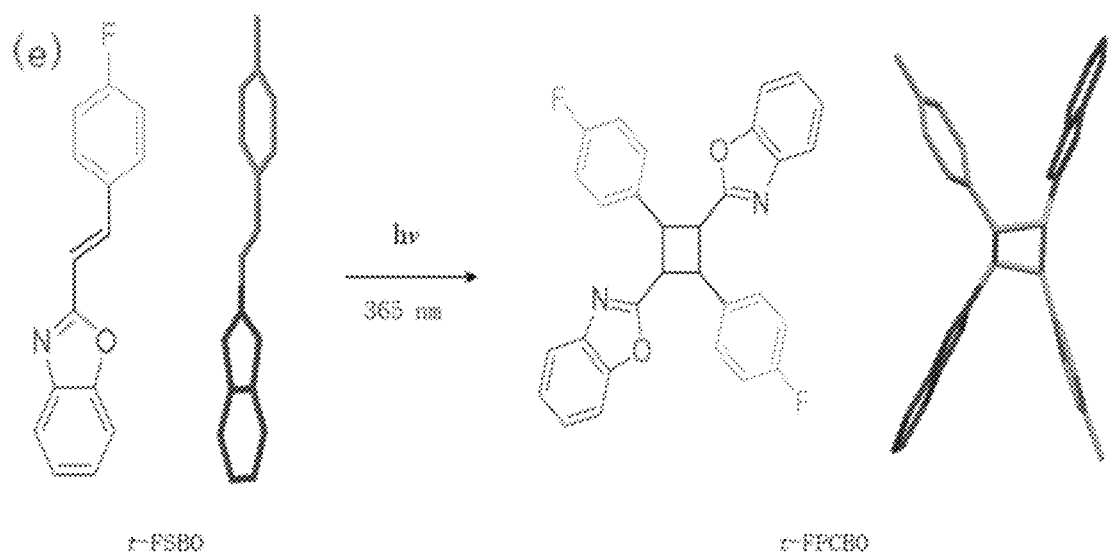
Figure 2:
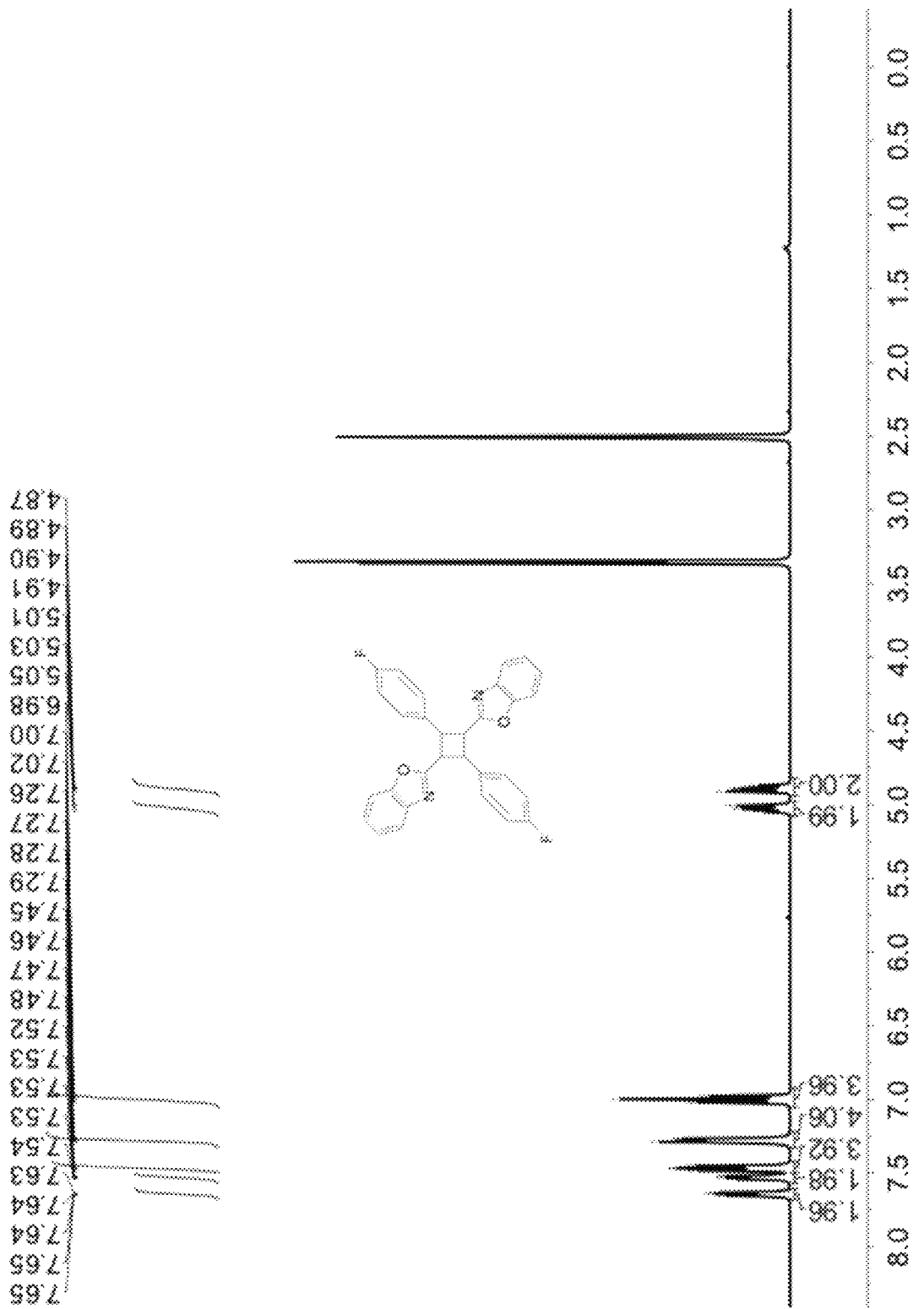
FIG. 2 shows $^1$H NMR (400 MHz, 298 K) spectrum of t-FPCBO in DMSO-$d_6$.
Figure 3:
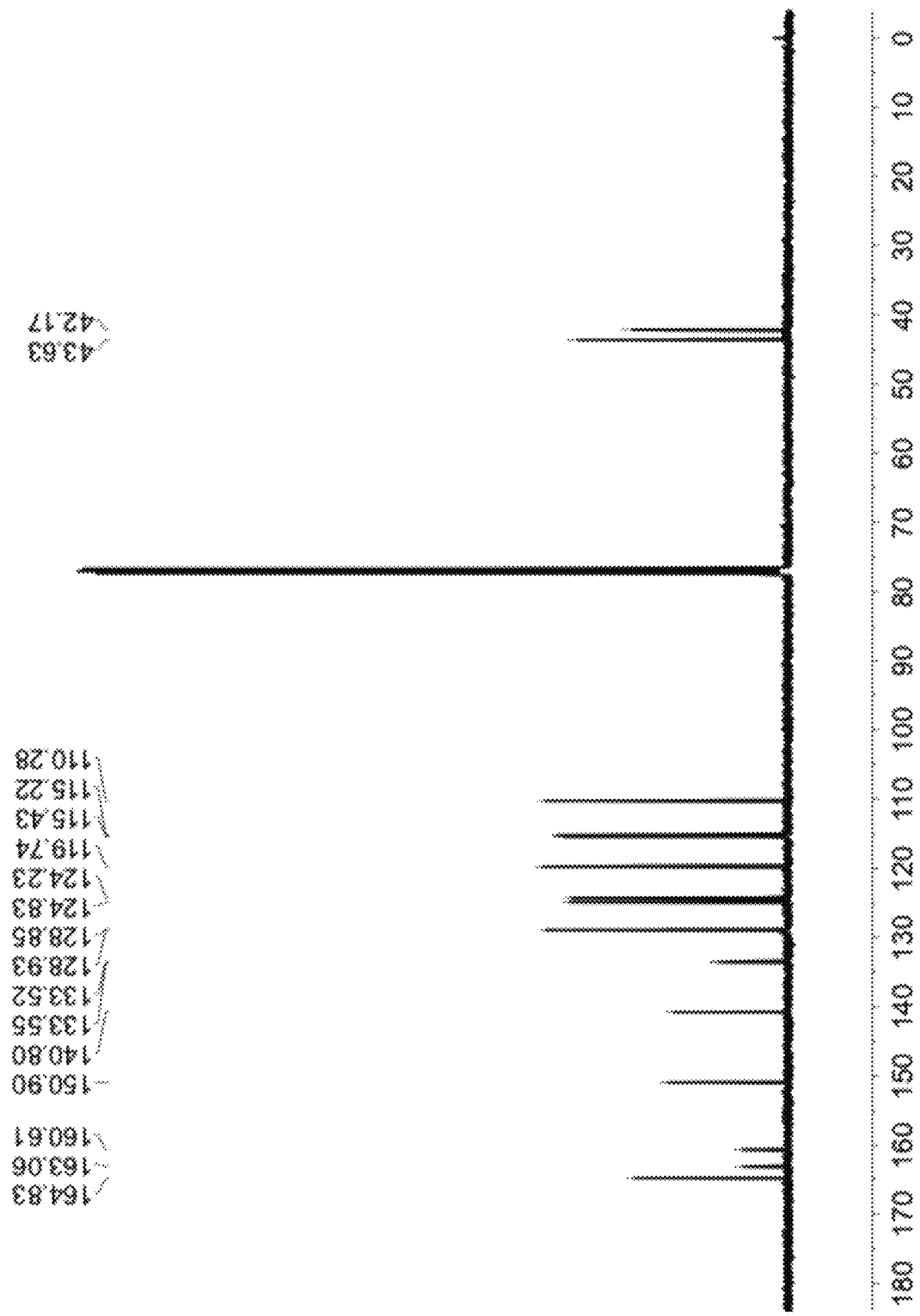
FIG. 3 shows $^{13}$C NMR (100 MHz, 298 K) spectrum of t-FPCBO in DMSO-$d_6$.
Figure 4:
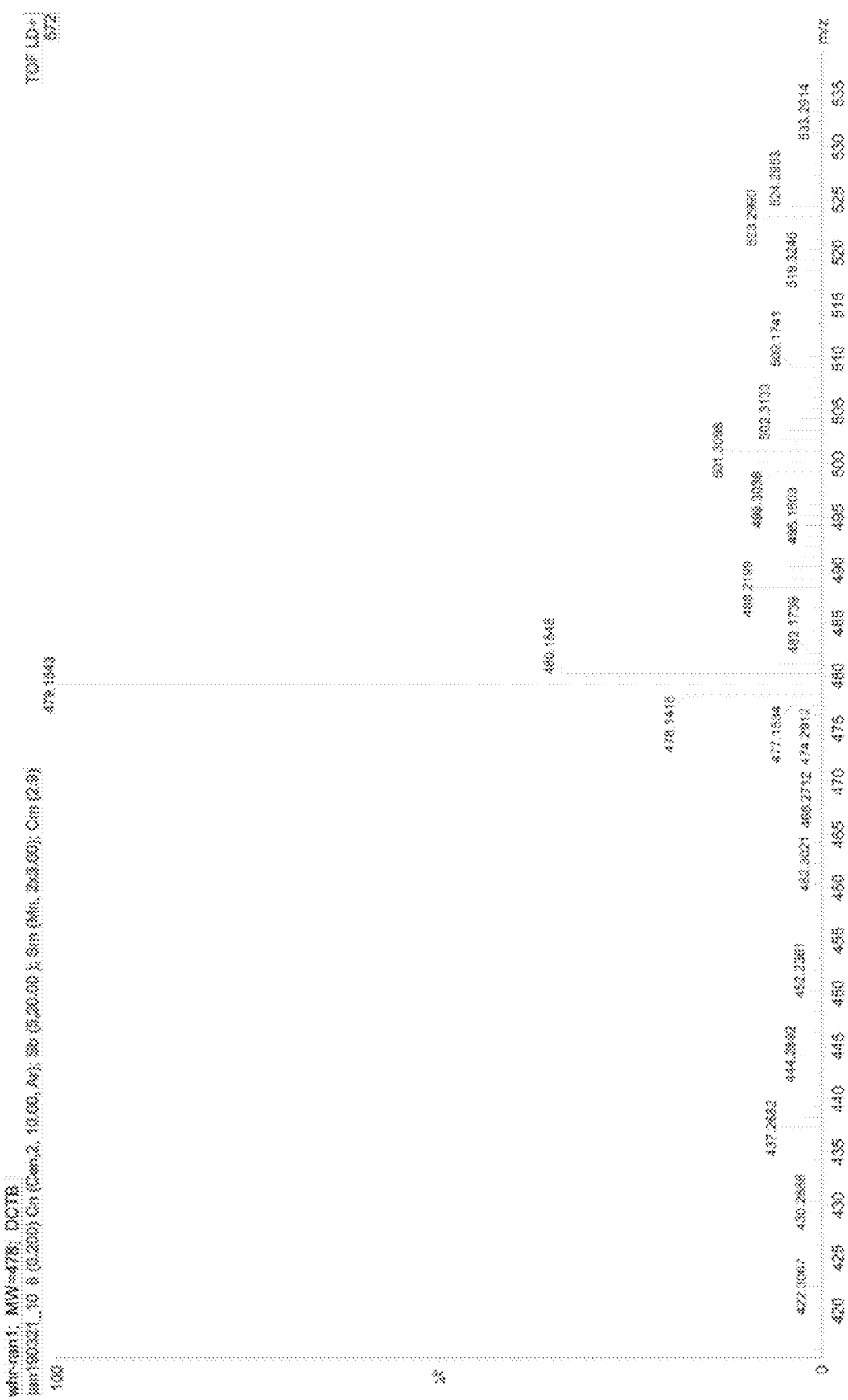
FIG. 4 shows MALDI-TOF spectrum of t-FPCBO.
Figure 5:
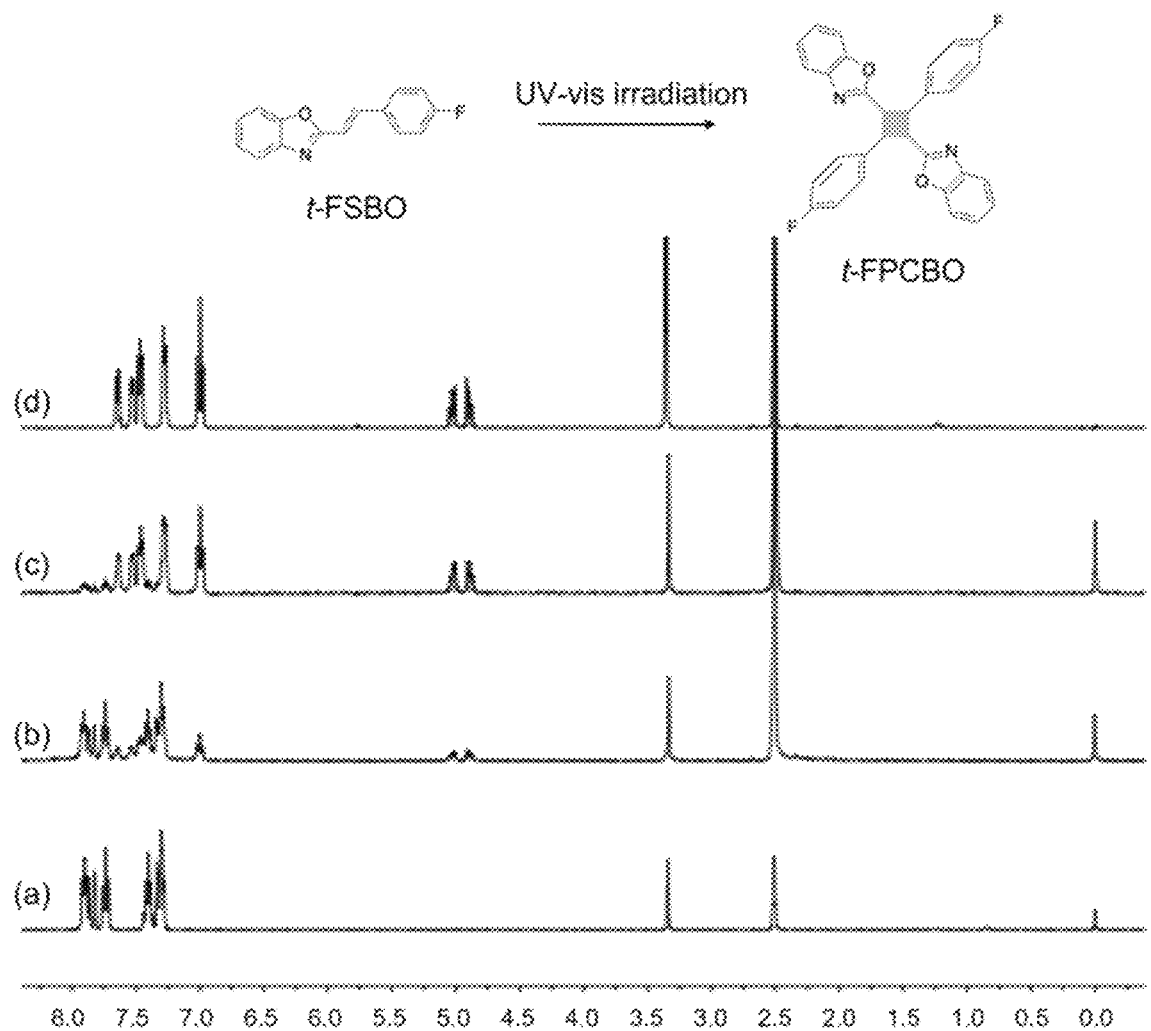
FIG. 5 shows $^1$H NMR spectra of the samples t-FSBO (400 MHz, 298 K), which were gained by dissolving the microcrystals (a) before and after being irradiated by 365 nm for (b) 2 min, (c) 4 min in DMSO-$d_6$. (d) $^1$H NMR spectrum of recrystallization of t-FSBO which was irradiated by 365 nm for 10 min in DMSO-$d_6$.
Figure 6:
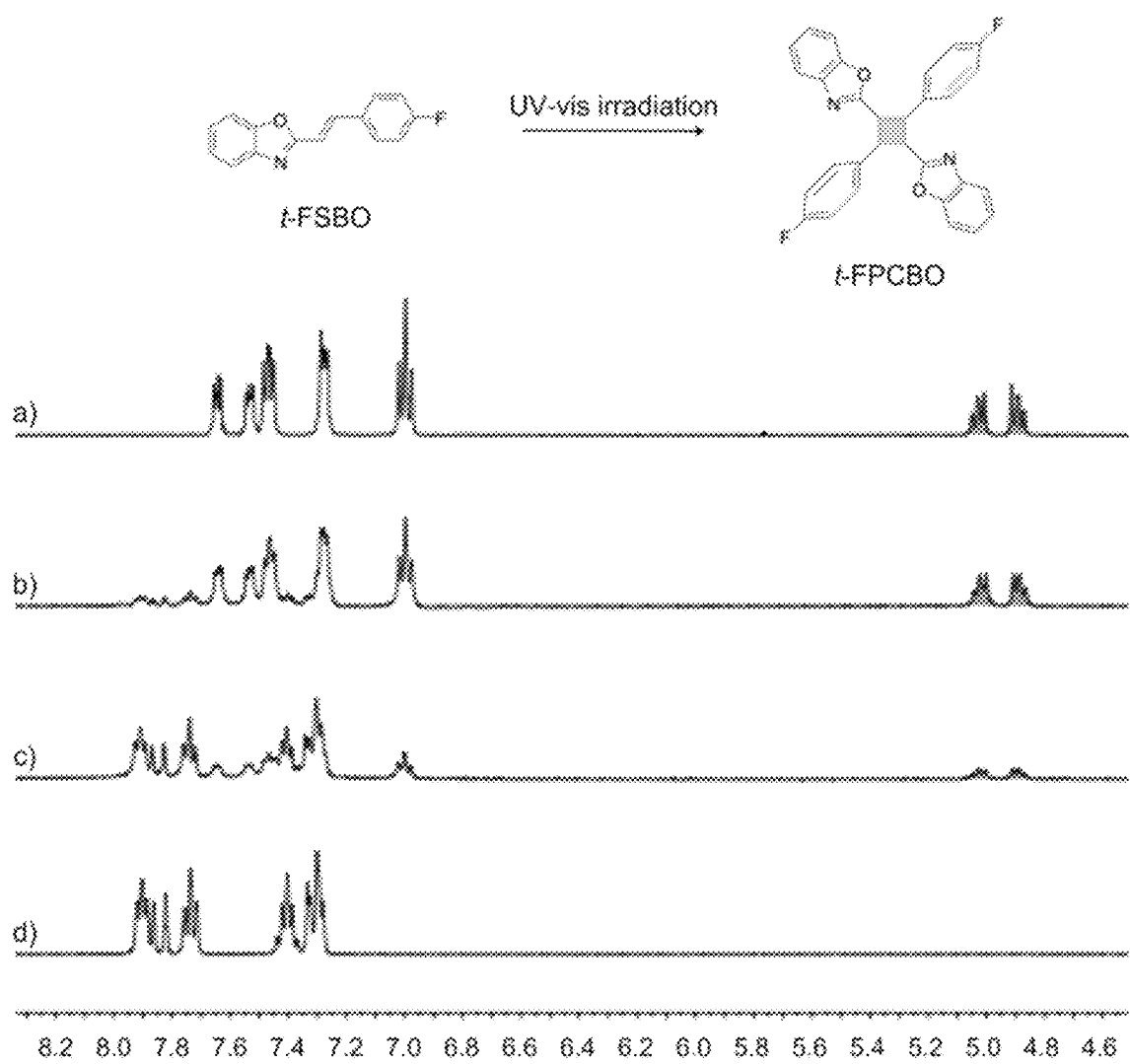
FIG. 6 shows enlarged $^1$H NMR spectra of the samples t-FSBO (400 MHz, 298 K), which were gained by dissolving the microcrystals (a) before and after being irradiated by 365 nm for (b) 2 min, (c) 4 min in DMSO-$d_6$. (d) $^1$H NMR spectrum of recrystallization of t-FSBO which was irradiated by 365 nm for 10 min in DMSO-$d_6$.
Figure 7:
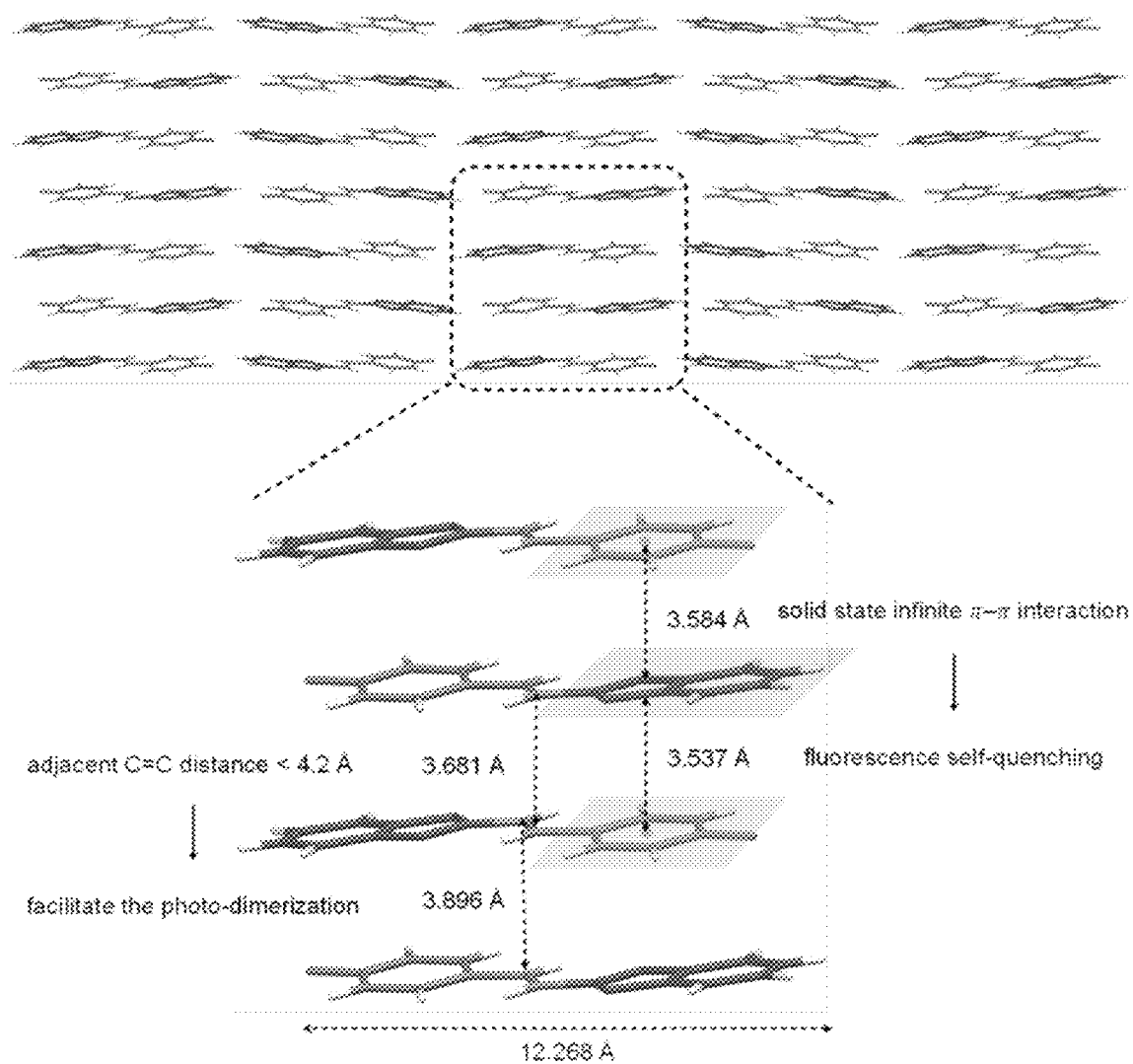
FIG. 7 shows Single crystal structure of t-FSBO and the distance between two adjacent parallel molecules.
Figure 8:
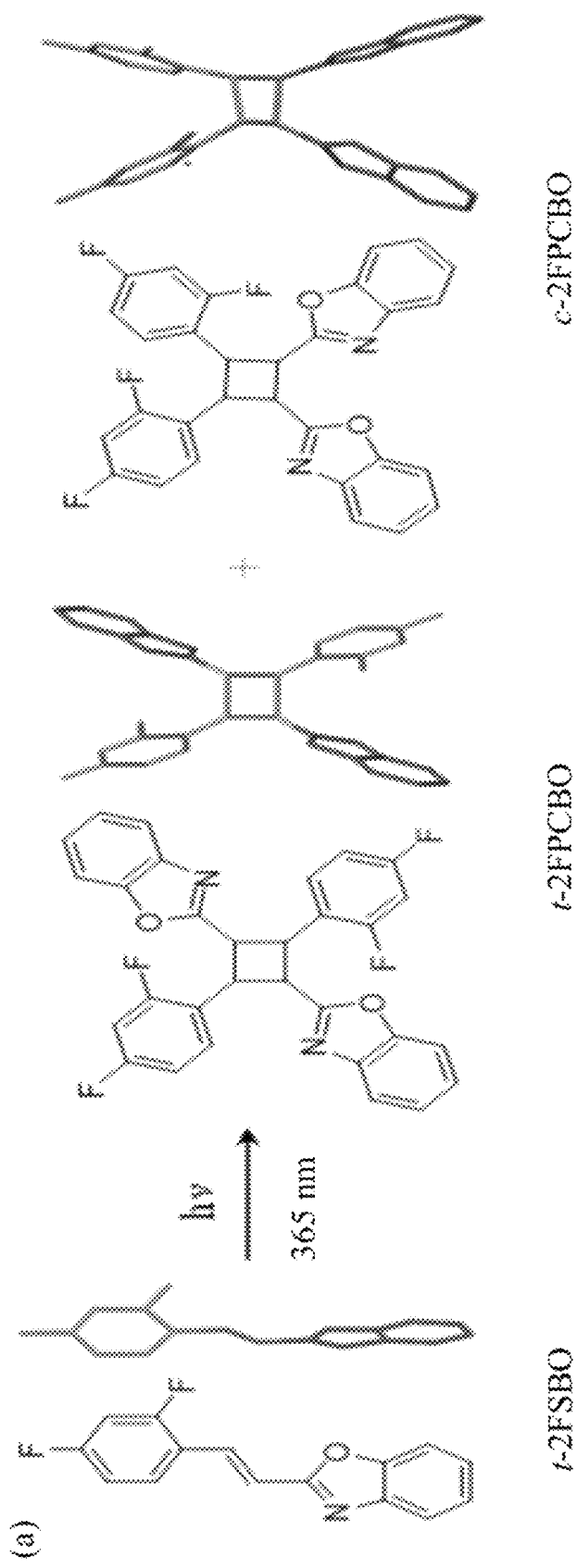
FIG. 8 shows (a) chemical and single crystal structures of t-2FSBO, t-2FPCBO, and c-2FPCBO. (b) PL spectra of t-2FPCBO in DMSO/water mixture with different water fractions ($f_w$). (c) Plots of relative $\alpha_{AIE}$ value versus $f_w$ of t-2FPCBO at 410 nm. $c=5\times10^{-4}$ M, $\lambda_{ex}=320$ nm. Inset: fluorescent photos of t-2FPCBO in DMSO/water mixture with 0% and 95% water fractions taken under 365 nm UV light irradiation. (d) PL spectra of c-2FPCBO in DMSO/water mixture with different water fractions ($f_w$). (e) Plots of relative $\alpha_{AIE}$ value versus $f_w$ of c-2FPCBO at 416 nm and 508 nm. $c=5\times10^{-4}$ M, $\lambda_{ex}=330$ nm. Inset: fluorescent photos of c-2FPCBO in DMSO/water mixture with 0%, 50%, and 95% water fractions taken under 365 nm UV light irradiation.
Figure 8:
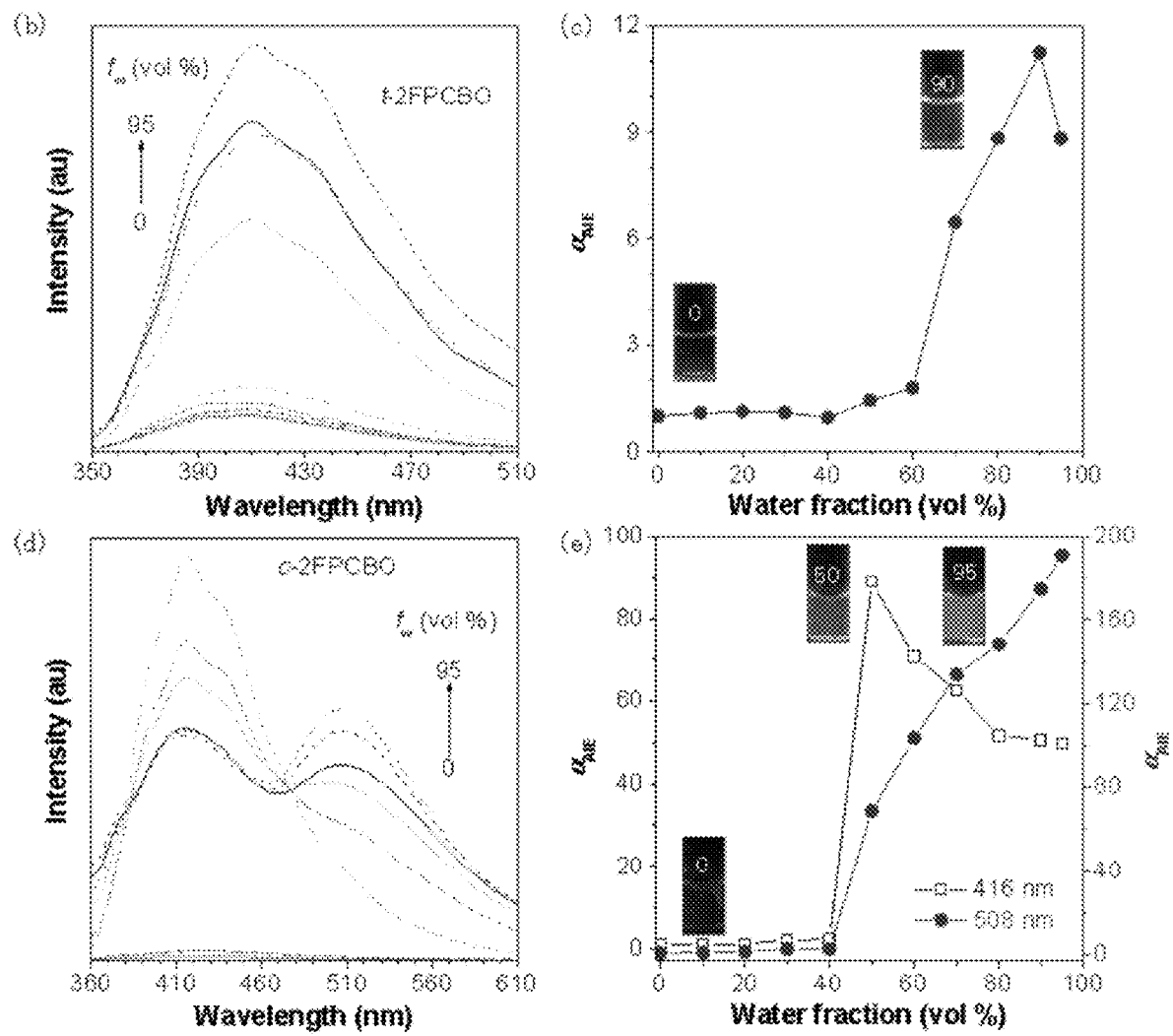
Figure 9:
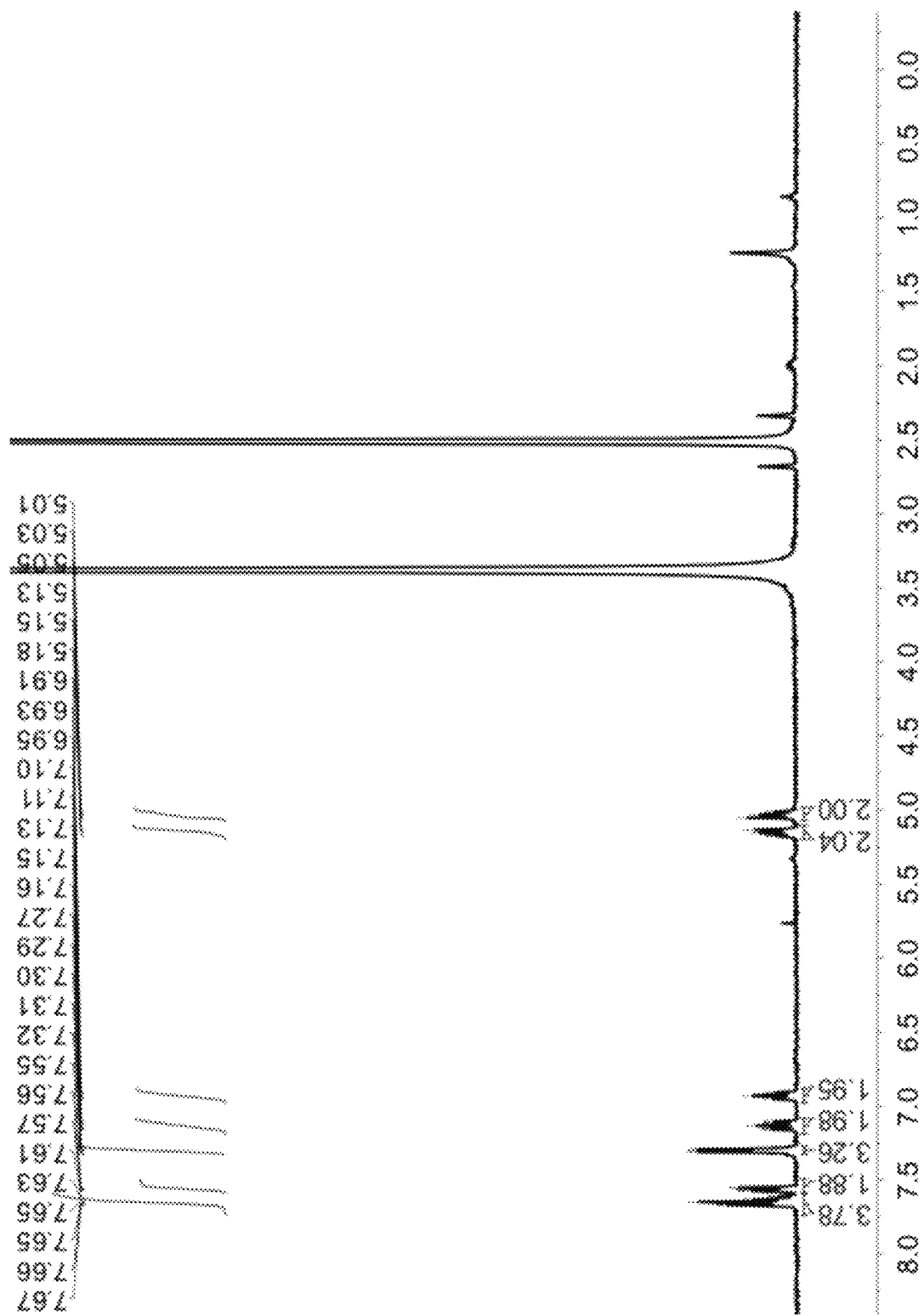
FIG. 9 shows $^1$H NMR (400 MHz, 298 K) spectrum of t-2FPCBO in DMSO-$d_6$.
Figure 10:
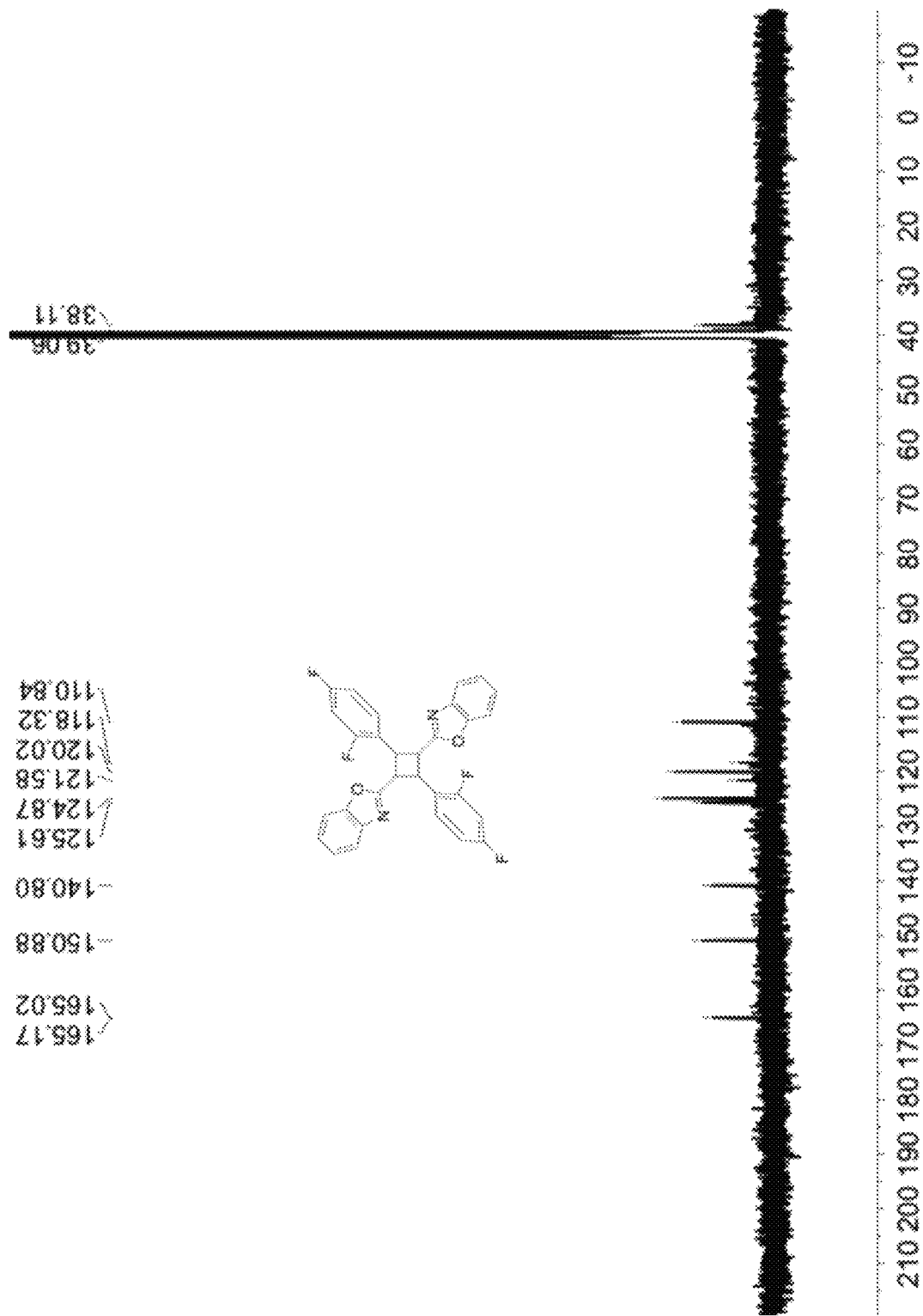
FIG. 10 shows $^{13}$C NMR (100 MHz, 298 K) spectrum of t-2FPCBO in DMSO-$d_6$.
Figure 11:
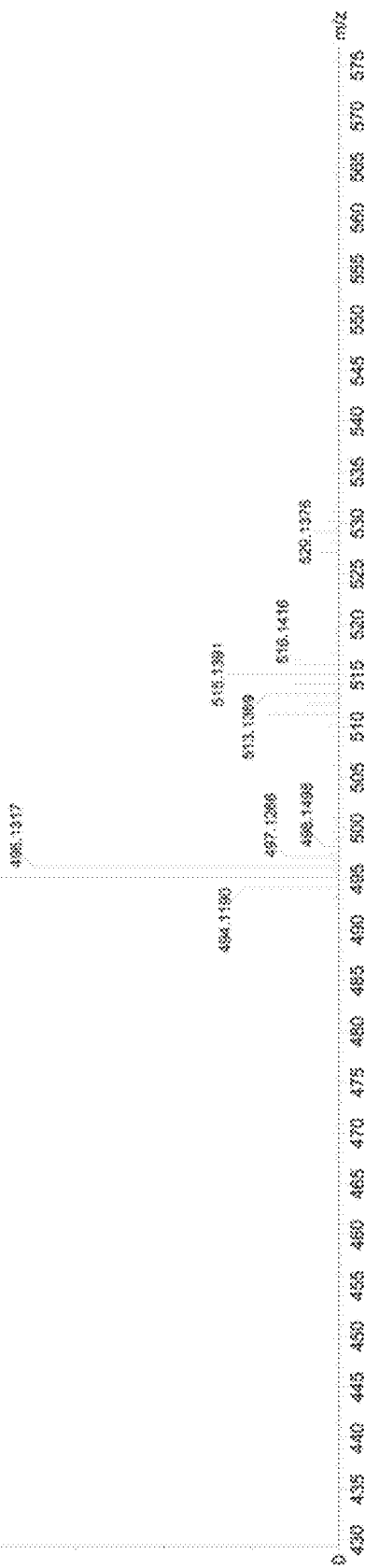
FIG. 11 shows MALDI-TOF spectrum of t-2FPCBO.
Figure 12:
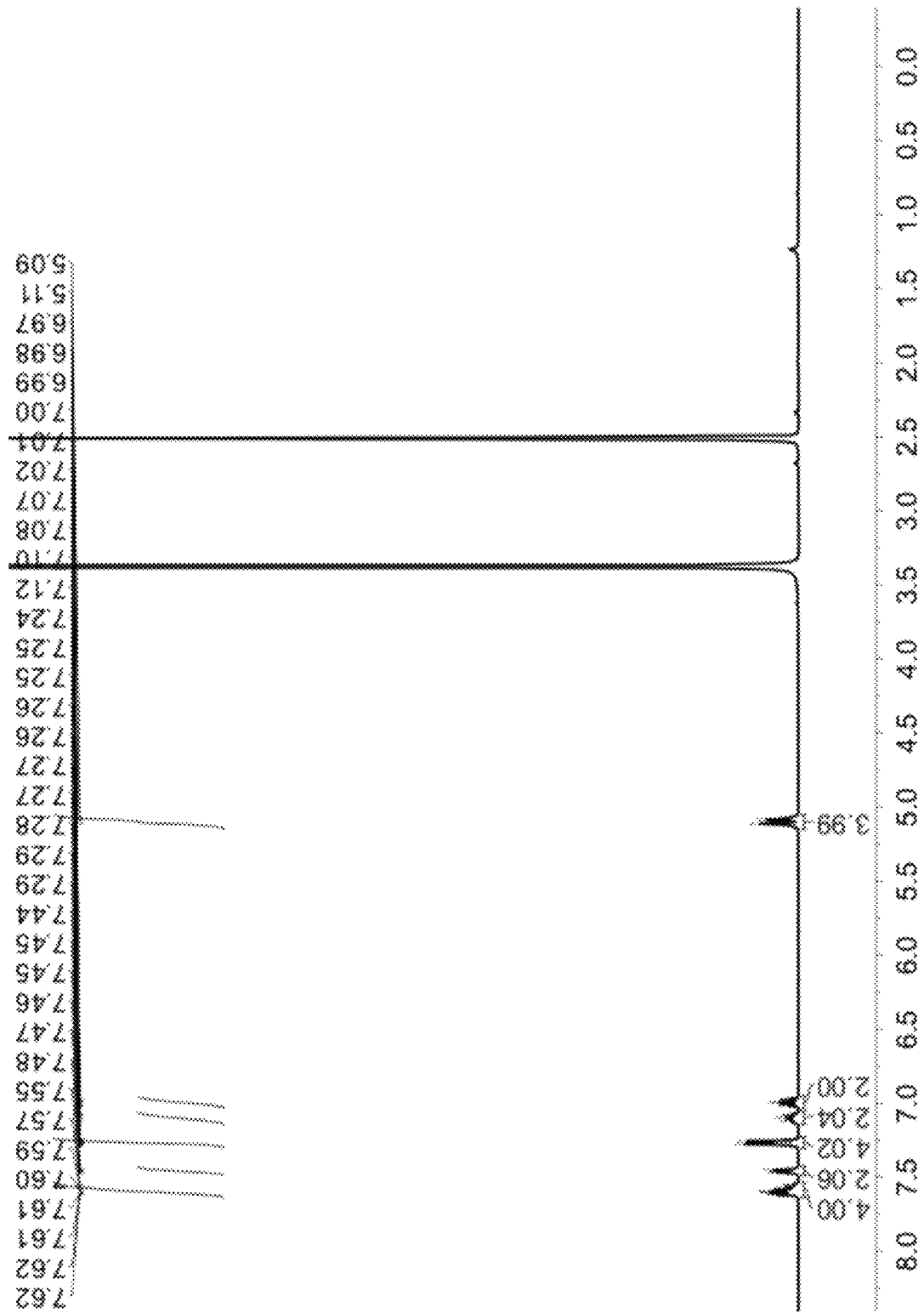
FIG. 12 shows $^1$H NMR (400 MHz, 298 K) spectrum of c-FPCBO in DMSO-$d_6$.
Figure 13:
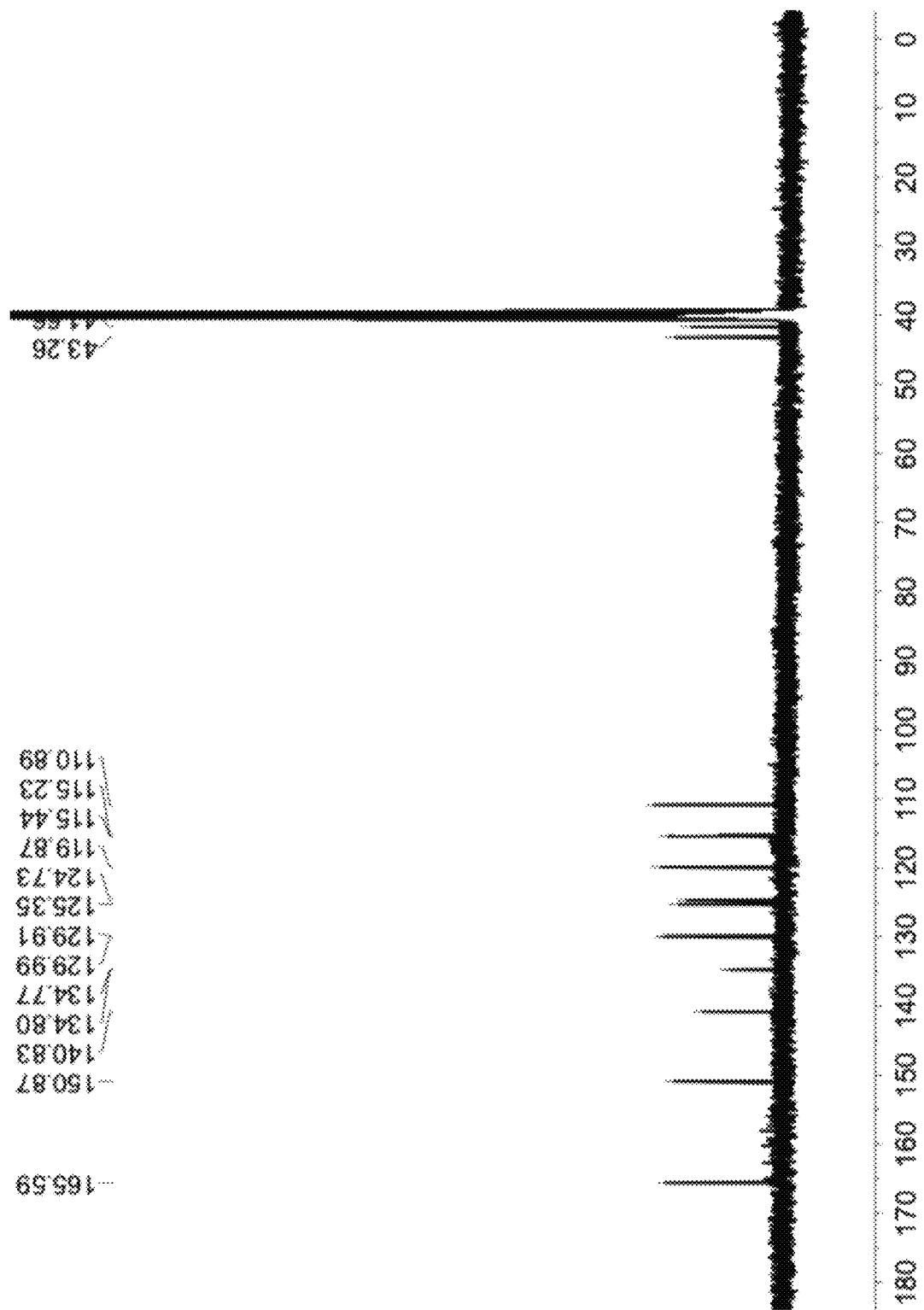
FIG. 13 shows $^{13}$C NMR (100 MHz, 298 K) spectrum of c-FPCBO in DMSO-$d_6$.
Figure 14:
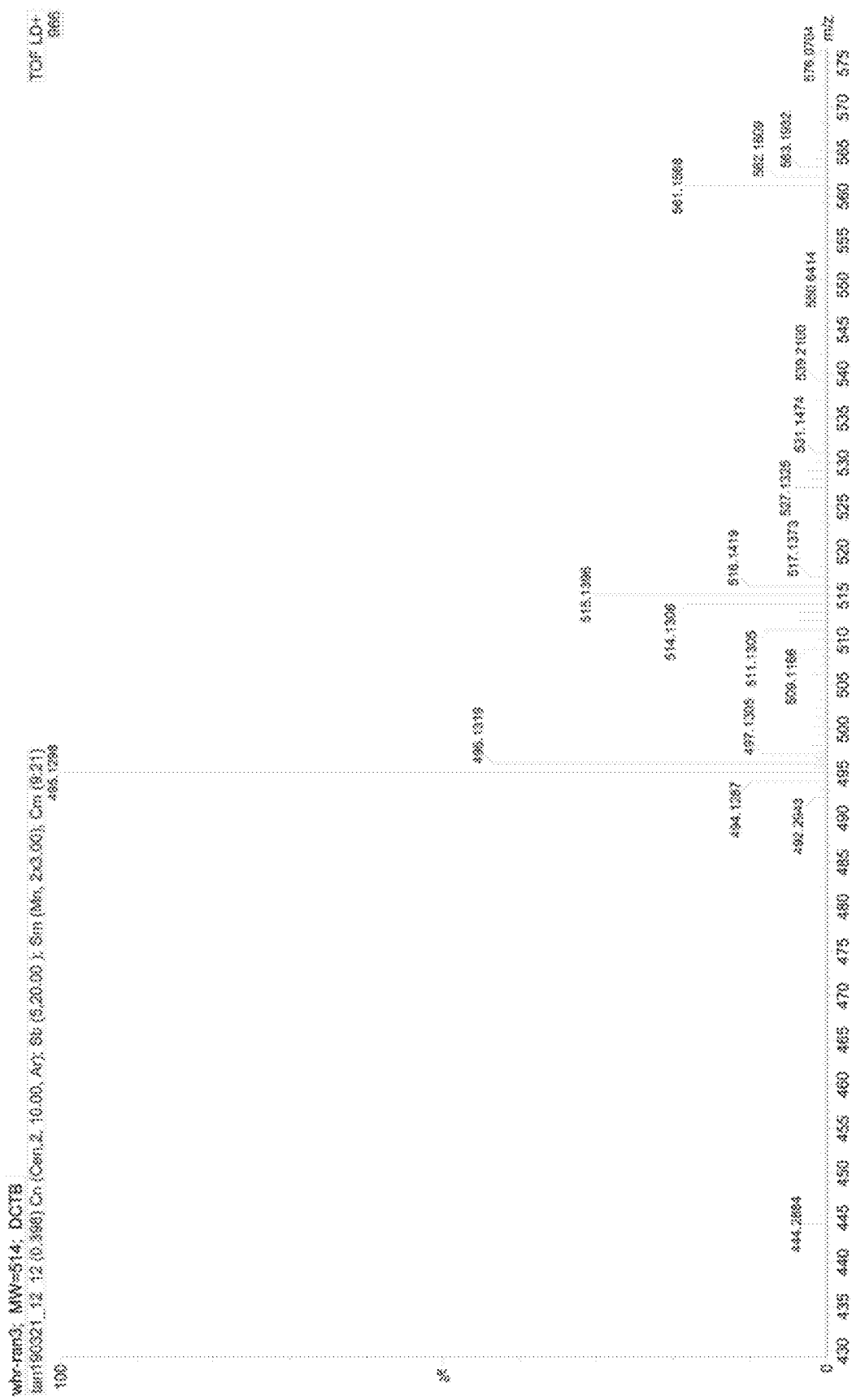
FIG. 14 shows MALDI-TOF spectrum of c-FPCBO.
Figure 15:
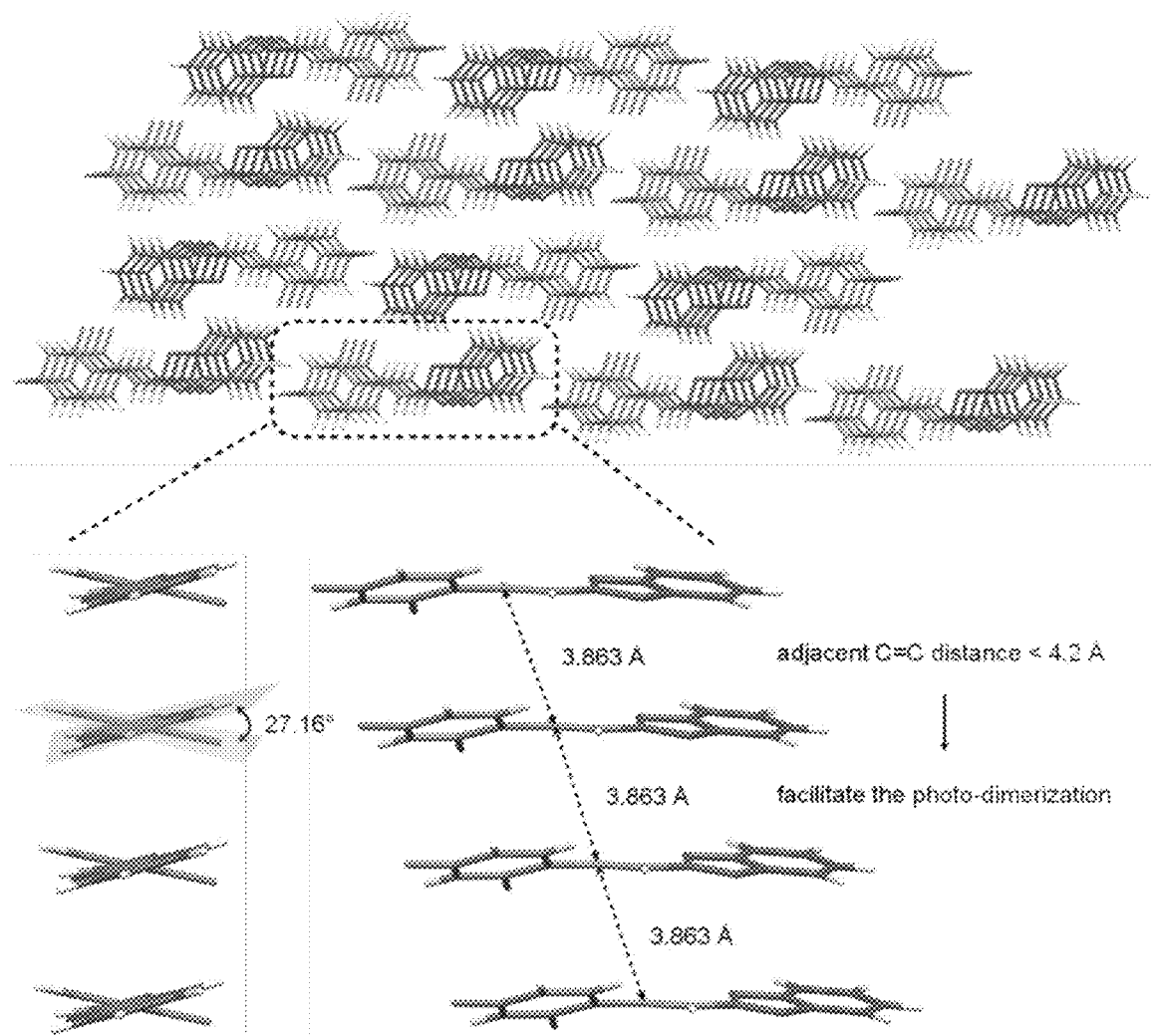
FIG. 15 shows single crystal structure of t-2FSBO and the distance between two adjacent parallel molecules.
Figure 16:
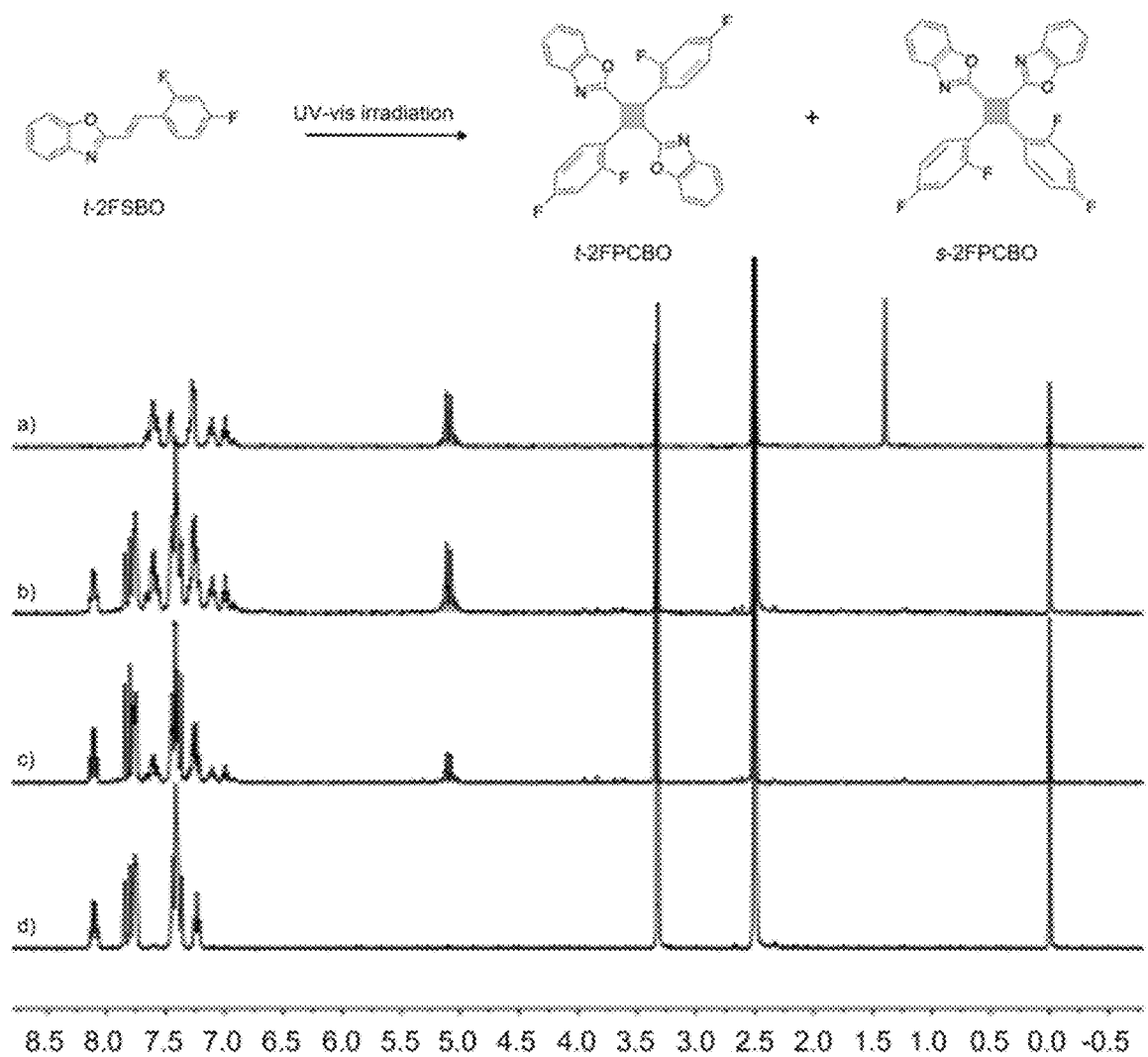
FIG. 16 shows $^1$H NMR spectra of the samples t-2FSBO (400 MHz, 298 K), which were gained by dissolving the microcrystals (a) before and after being irradiated by 365 nm for (b) 2 min, (c) 4 min in DMSO-$d_6$. (d) $^1$H NMR spectrum of recrystallization of t-2FSBO which was irradiated by 365 nm for 10 min in DMSO-$d_6$.
Figure 17:
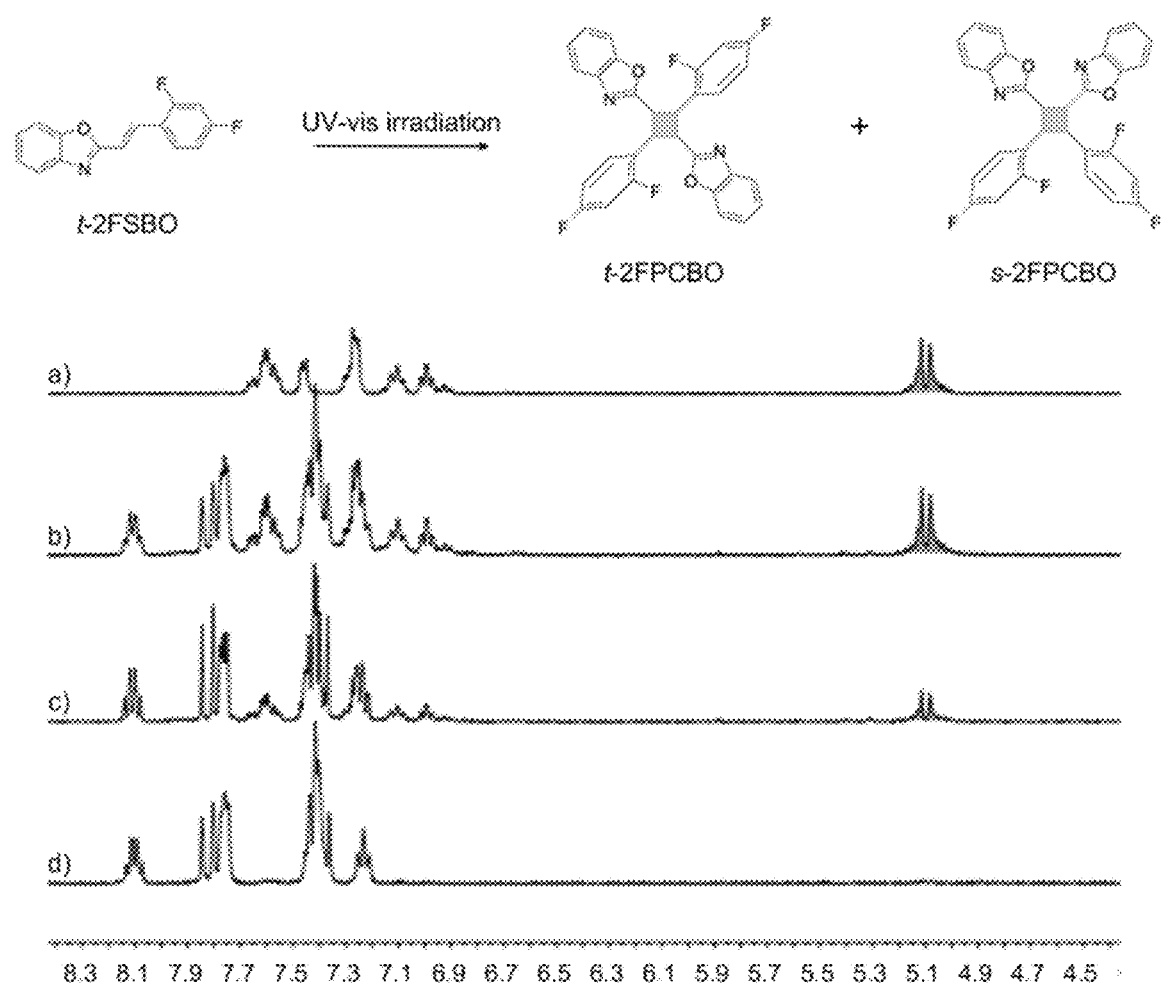
FIG. 17 shows Enlarged $^1$H NMR spectra of the samples t-2FSBO (400 MHz, 298 K), which were gained by dissolving the microcrystals (a) before and after being irradiated by 365 nm for (b) 2 min, (c) 4 min in DMSO-$d_6$. (d) $^1$H NMR spectrum of recrystallization of t-2FSBO which was irradiated by 365 nm for 10 min in DMSO-$d_6$.
Figure 18:
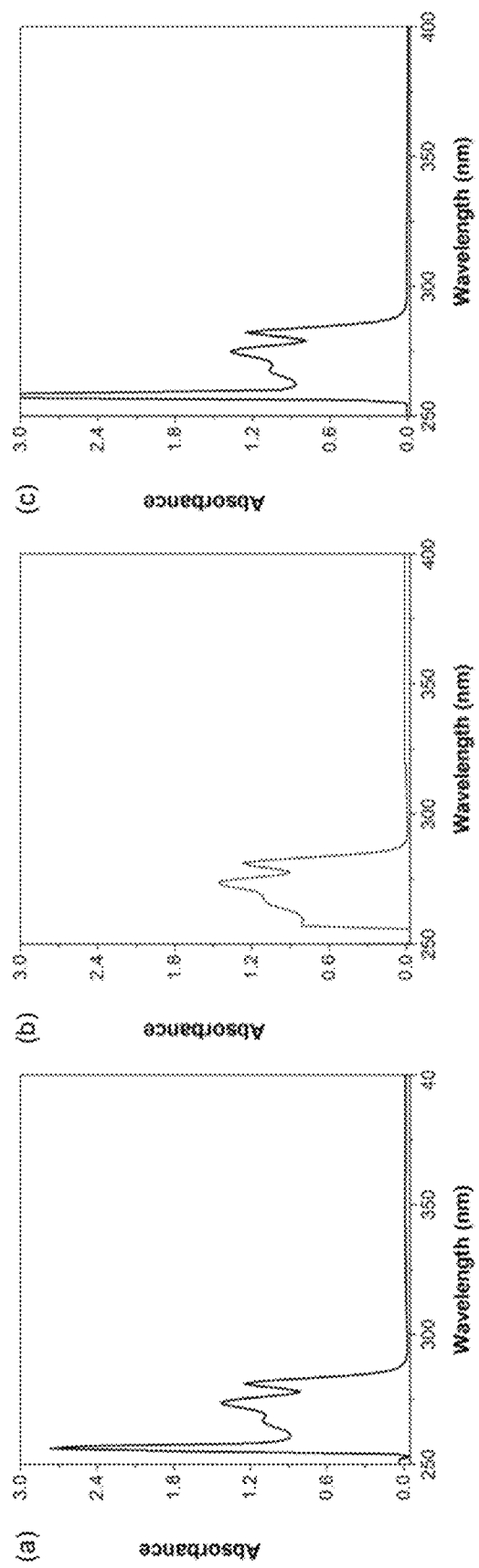
FIG. 18 shows UV-vis absorption spectra of (a) t-FPCBO, (b) t-2FPCBO, and (c) c-2FPCBO in $CH_2Cl_2$, $c=1.0\times10^{-5}$ M.
Figure 19:
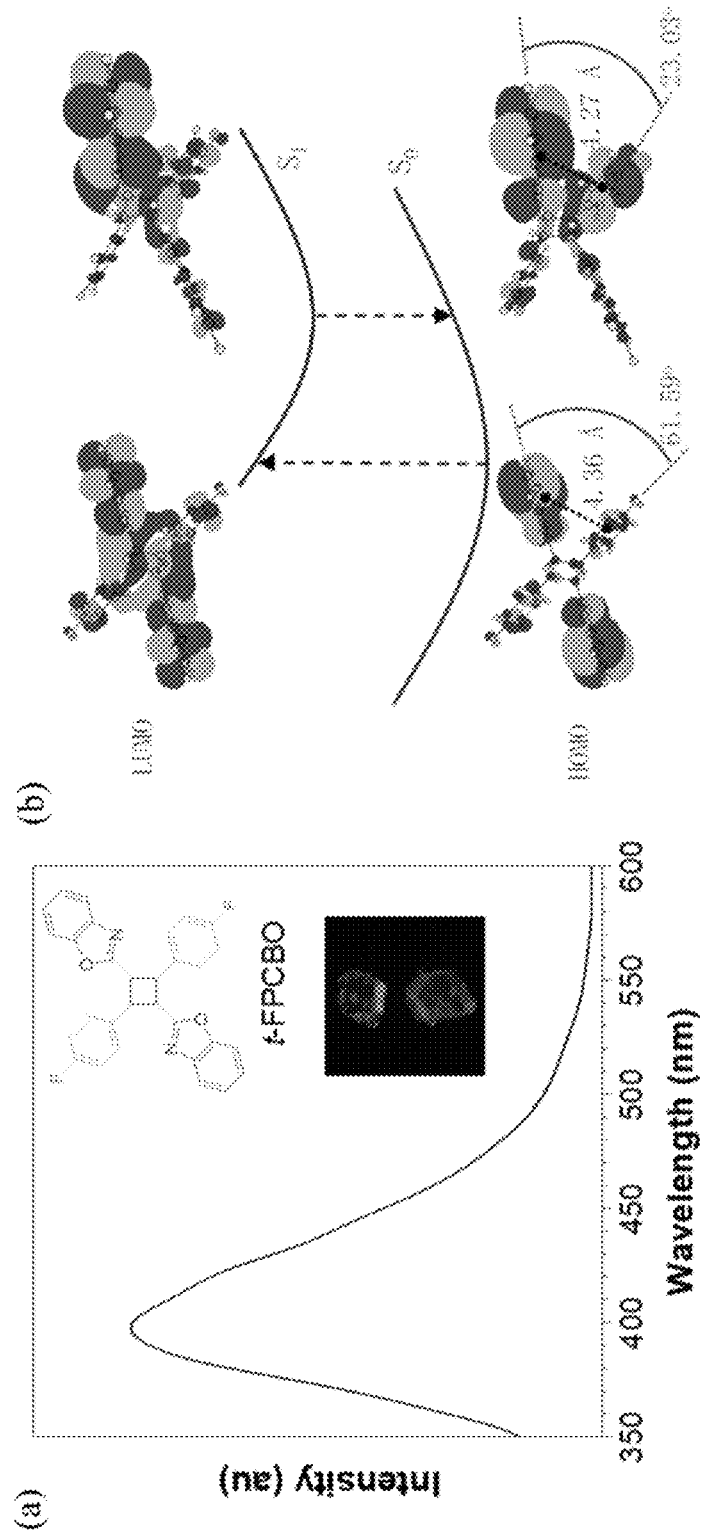
FIG. 19 shows (a) PL spectrum of t-FPCBO emissive crystals. Inset: fluorescent photos of the crystals under 365 nm UV light irradiation. (b) Electron cloud distribution, energy levels of t-FPCBO in the ground and excited state calculated by TD-DFT B3LYP/6-31G(d), Gaussian 09 program.
Figure 20:
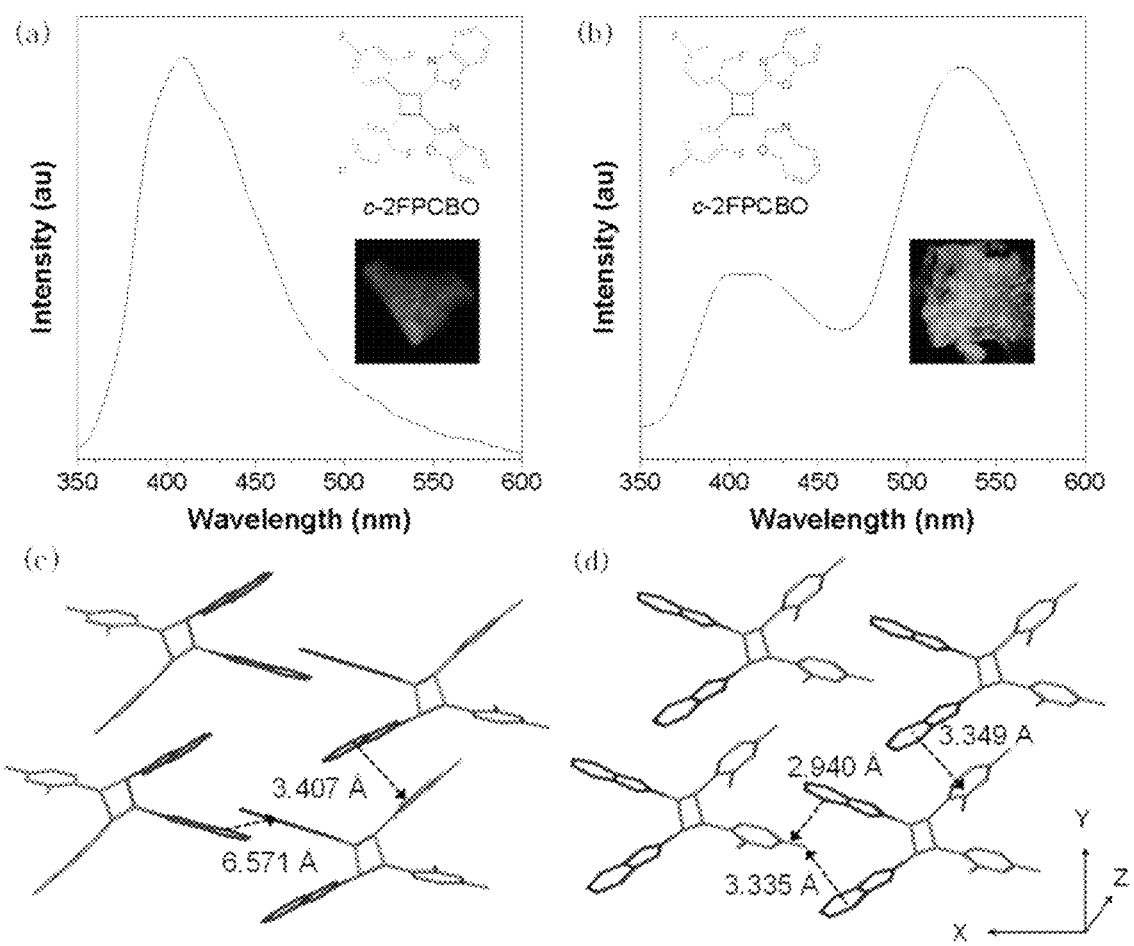
FIG. 20 shows (a) PL spectra of c-2FPCBO blue emissive and (b) c-2FPCBO yellow emissive crystals. Inset: fluorescent photos of these two crystals under 365 nm UV light irradiation. Crystal packing diagrams of (c) c-2FPCBO blue emissive and (d) c-2FPCBO yellow emissive crystals.

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10%, ±7%, ±5%, ±3%, ±1%, or ±0% variation from the nominal value unless otherwise indicated or inferred.

It should be understood that the order of steps or order for performing certain actions is immaterial so long as the present teachings remain operable. Moreover, two or more steps or actions may be conducted simultaneously.

As used herein, "halo", "halide", or "halogen" refers to fluoro, chloro, bromo, and iodo.

As used herein, "alkyl" refers to a straight-chain or branched saturated hydrocarbon group. Examples of alkyl groups include methyl (Me), ethyl (Et), propyl (e.g., n-propyl and isopropyl), butyl (e.g., n-butyl, iso-butyl, sec-butyl, tert-butyl), pentyl groups (e.g., 1-methylbutyl, 2-methylbutyl, iso-pentyl, tert-pentyl, 1,2-dimethylpropl, neopentyl, and 1-ethylpropyl), hexyl groups, and the like. In various embodiments, an alkyl group can have 1 to 40 carbon atoms (i.e., $C_1$-$C_{40}$ alkyl group), for example, 1-30 carbon atoms (i.e., $C_1$-$C_{30}$ alkyl group). In some embodiments, an alkyl group can have 1 to 6 carbon atoms, and can be referred to as a "lower alkyl group." Examples of lower alkyl groups include methyl, ethyl, propyl (e.g., n-propyl and z'-propyl), and butyl groups (e.g., n-butyl, z'-butyl, sec-butyl, tert-butyl). In some embodiments, alkyl groups can be substituted as described herein. An alkyl group is generally not substituted with another alkyl group, an alkenyl group, or an alkynyl group.

The term "aralkyl" is art-recognized and refers to an alkyl group substituted with an aryl group (e.g., an aromatic or heteroaromatic group).

As used herein, "cycloalkyl" by itself or as part of another substituent means, unless otherwise stated, a monocyclic hydrocarbon having between 3-12 carbon atoms in the ring system and includes hydrogen, straight chain, branched chain, and/or cyclic substituents. Exemplary cycloalkyls include cyclopropyl, cyclobutyl, cyclopentyl, cyclohexyl, cycloheptyl, and the like.

As used herein, "alkenyl" refers to a straight-chain or branched alkyl group having one or more carbon-carbon double bonds. Examples of alkenyl groups include ethenyl, propenyl, butenyl, pentenyl, hexenyl, butadienyl, pentadienyl, hexadienyl groups, and the like. The one or more carbon-carbon double bonds can be internal (such as in 2-butene) or terminal (such as in 1-butene). In various embodiments, an alkenyl group can have 2 to 40 carbon atoms (i.e., $C_2$-$C_{40}$ alkenyl group), for example, 2 to 20 carbon atoms (i.e., $C_2$-$C_{20}$ alkenyl group). In some embodiments, alkenyl groups can be substituted as described herein. An alkenyl group is generally not substituted with another alkenyl group, an alkyl group, or an alkynyl group.

As used herein, a "fused ring" or a "fused ring moiety" refers to a polycyclic ring system having at least two rings where at least one of the rings is aromatic and such aromatic ring (carbocyclic or heterocyclic) has a bond in common with at least one other ring that can be aromatic or non-aromatic, and carbocyclic or heterocyclic. These polycyclic ring systems can be highly p-conjugated and optionally substituted as described herein.

As used herein, "heteroatom" refers to an atom of any element other than carbon or hydrogen and includes, for example, nitrogen, oxygen, silicon, sulfur, phosphorus, and selenium.

As used herein, "aryl" refers to an aromatic monocyclic hydrocarbon ring system or a polycyclic ring system in which two or more aromatic hydrocarbon rings are fused (i.e., having a bond in common with) together or at least one aromatic monocyclic hydrocarbon ring is fused to one or more cycloalkyl and/or cyclohteroalkyl rings. An aryl group can have 6 to 24 carbon atoms in its ring system (e.g., $C_6$-$C_{24}$ aryl group), which can include multiple fused rings. In some embodiments, a polycyclic aryl group can have 8 to 24 carbon atoms. Any suitable ring position of the aryl group can be covalently linked to the defined chemical structure. Examples of aryl groups having only aromatic carbocyclic ring(s) include phenyl, 1-naphthyl (bicyclic), 2-naphthyl (bicyclic), anthracenyl (tricyclic), phenanthrenyl (tricyclic), pentacenyl (pentacyclic), and like groups. Examples of polycyclic ring systems in which at least one aromatic carbocyclic ring is fused to one or more cycloalkyl and/or cycloheteroalkyl rings include, among others, benzo derivatives of cyclopentane (i.e., an indanyl group, which is a 5,6-bicyclic cycloalkyl/aromatic ring system), cyclohexane (i.e., a tetrahydronaphthyl group, which is a 6,6-bicyclic cycloalkyl/aromatic ring system), imidazoline (i.e., a benzimidazolinyl group, which is a 5,6-bicyclic cycloheteroalkyl/aromatic ring system), and pyran (i.e., a chromenyl group, which is a 6,6-bicyclic cycloheteroalkyl/aromatic ring system). Other examples of aryl groups include benzodioxanyl, benzodioxolyl, chromanyl, indolinyl groups, and the like. In some embodiments, aryl groups can be optionally substituted as described herein. The aryl ring may be substituted at one or more positions with such substituents as described herein, as for example, halogen, alkyl, aralkyl, alkenyl, alkynyl, cycloalkyl, hydroxyl, aryloxy, heteroaryloxy, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like. In some embodiments, an aryl group can have one or more halogen substituents, and can be referred to as a "haloaryl" group. Perhaloaryl groups, i.e., aryl groups where all of the hydrogen atoms are replaced with halogen atoms (e.g., —C$_6$F$_5$), are included within the definition of "haloaryl." In certain embodiments, an aryl group is substituted with another aryl group and can be referred to as a biaryl group. Each of the aryl groups in the biaryl group can be optionally substituted as disclosed herein.

The term "aryloxy" refers to a monovalent group of formula —O-aryl.

The term "heteroaryloxy" refers to a monovalent group of formula —O-heteroaryl.

As used herein, "heteroaryl" refers to an aromatic monocyclic ring system containing at least one ring heteroatom selected from oxygen (O), nitrogen (N), sulfur (S), silicon (Si), and selenium (Se) or a polycyclic ring system where at least one of the rings present in the ring system is aromatic and contains at least one ring heteroatom. Polycyclic heteroaryl groups include those having two or more heteroaryl rings fused together, as well as those having at least one monocyclic heteroaryl ring fused to one or more aromatic carbocyclic rings, non-aromatic carbocyclic rings, and/or non-aromatic cycloheteroalkyl rings. A heteroaryl group, as a whole, can have, for example, 5 to 24 ring atoms and contain 1-5 ring heteroatoms (i.e., 5-20 membered heteroaryl group). The heteroaryl group can be attached to the defined chemical structure at any heteroatom or carbon atom that results in a stable structure. Generally, heteroaryl rings do not contain O—O, S—S, or S—O bonds. However, one or more N or S atoms in a heteroaryl group can be oxidized (e.g., pyridine N-oxide thiophene S-oxide, thiophene S,S-dioxide). Examples of heteroaryl groups include, for example, the 5- or 6-membered monocyclic and 5-6 bicyclic ring systems shown below: where T is O, S, NH, N-alkyl, N-aryl, N-(arylalkyl) (e.g., N-benzyl), SiH$_2$, SiH(alkyl), Si(alkyl)$_2$, SiH(arylalkyl), Si(arylalkyl)$_2$, or Si(alkyl)(arylalkyl). Examples of such heteroaryl rings include pyrrolyl, furyl, thienyl, pyridyl, pyrimidyl, pyridazinyl, pyrazinyl, triazolyl, tetrazolyl, pyrazolyl, imidazolyl, isothiazolyl, thiazolyl, thiadiazolyl, isoxazolyl, oxazolyl, oxadiazolyl, indolyl, isoindolyl, benzofuryl, benzothienyl, quinolyl, 2-methylquinolyl, isoquinolyl, quinoxalyl, quinazolyl, benzotriazolyl, benzimidazolyl, benzothiazolyl, benzisothiazolyl, benzisoxazolyl, benzoxadiazolyl, benzoxazolyl, cinnolinyl, 1H-indazolyl, 2H-indazolyl, indolizinyl, isobenzofuyl, naphthyridinyl, phthalazinyl, pteridinyl, purinyl, oxazolopyridinyl, thiazolopyridinyl, imidazopyridinyl, furopyridinyl, thienopyridinyl, pyridopyrimidinyl, pyridopyrazinyl, pyridopyridazinyl, thienothiazolyl, thienoxazolyl, thienoimidazolyl groups, and the like. Further examples of heteroaryl groups include 4,5,6,7-tetrahydroindolyl, tetrahydroquinolinyl, benzothienopyridinyl, benzofuropyridinyl groups, and the like. In some embodiments, heteroaryl groups can be optionally substituted as described herein. The heterocyclic ring may be substituted at one or more positions with such substituents as described herein, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like. A "nitrogen containing heteroaryl" is a hetoeraryl as defined herein with an aromatic ring system having at least one ring nitrogen (N).

The term "optionally substituted" refers to a chemical group, such as alkyl, cycloalkyl, aryl, heteroaryl, and the like, wherein one or more hydrogen may be replaced with a with a substituent as described herein, for example, halogen, azide, alkyl, aralkyl, alkenyl, alkynyl, cycloalkyl, hydroxyl, aryloxy, heteroaryloxy, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, or the like The term "substantially crystalline" refers to compositions or compounds with at least 70% by weight, at least 75% by weight, at least 80% by weight, at least 85% by weight, at least 90 by weight, at least 95% by weight, at least 96% by weight, at least 97% by weight, at least 98% by weight, at least 99% by weight, at least 99.5% by weight, or more of the composition or compound is present in crystalline form. The compositions or compounds can exist in a single crystalline form or more than one crystalline form. In certain embodiments, the composition or compound has at least 70% by weight, at least 75% by weight, at least 80% by weight, at least 85% by weight, at least 90 by weight, at least 95% by weight, at least 96% by weight, at least 97% by weight, at least 98% by weight, at least 99% by weight, at least 99.5% by weight, or more of the composition or compound present in a single crystalline form. The degree (%) of crystallinity may be determined by the skilled person using X-ray powder diffraction (MOD). Other techniques, such as solid state NMR, FT-IR, Raman spectroscopy, differential scanning calorimetry (DSC) and microcalorimetry, may also be used.

The term "substantially pure" when used in connection with a sample of a compound or composition described herein means that the sample contains at least 60% by weight of the compound or composition. In certain embodiments, the sample contains at least 70% by weight of the compound or composition; at least 75% by weight of the compound or composition; at least 80% by weight of the compound or composition; at least 85% by weight of the compound or composition; at least 90% by weight of the compound or composition; at least 95% by weight of the compound or composition; at least 98% by weight of the compound or composition; at least 99% by weight of the compound or composition; at least 99.5% by weight of the compound or composition; at least 99.9% by weight of the compound or composition or greater.

The representation "<img>" as used herein in connection to chemical a group or moiety is intended to represent the covalent bond that the aforementioned chemical group or moiety is covalently bonded to another chemical group or moiety.

The term "$\lambda_{ex}$" as used herein refers to the excitation wavelength.

The term "$\lambda_{em}$" as used herein refers to the emission wavelength.

Provided herein are compounds that exhibit multifunctional photoresponsive properties, such at least one of AIE and macroscopic actuation. The multifunctional properties of the compounds can be generated by irradiation with light, such as UV light, of a crystal comprising a first compound that exhibits ACQ thereby causing the first compound to undergo photodimerization by [2+2] cycloaddition thereby yielding a second compound exhibiting AIE properties and concomitant mechanical actuation as a result of a large change in volume of the second compound.

In certain embodiments, the first compound has Formula 3:

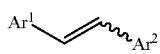

3 or a conjugate salt thereof, wherein each of $Ar^1$ and $Ar^2$ are independently aryl or heteroaryl.

In certain embodiments, $Ar^1$ is optionally substituted phenyl and $Ar^2$ is optionally substituted heteroaryl. In certain embodiments, $Ar^1$ is optionally substituted phenyl and $Ar^2$ is optionally substituted 2-benzoxazolyl.

The use of "<img>" bond attaching $Ar^2$ to the olefin indicates that $Ar^2$ can be present on either face of the olefin, i.e., the olefin shown in the compound described herein can be a cis olefin or a trans olefin. In certain embodiments, the olefin has a trans configuration.

In certain embodiments, the first compound is substantially pure and/or substantially crystalline. In certain embodiments, the first compound is substantially pure and substantially crystalline.

In certain embodiments, the first compound has Formula 1:

1 or a conjugate salt thereof, wherein each of m and n are independently a whole number selected from 0-4; and each of $R^1$ and $R^2$ is independently hydrogen, halide, nitrile, nitro, OR, $N(R)_2$, $O(C=O)R$, $N(R)(C=O)R$, $(C=O)R$, $CO_2R$, CHO, $(C=O)NR(R)_2$, $N(R)(C=O)NR(R)_2$, $O(C=O)NR(R)_2$, $N(R)(C=O)OR$, $—SO_2R$, $—SO_2NR_2$, alkyl, cycloalkyl, alkenyl, alkynyl, aryl, heterocycloalkyl, heteroaryl, or $—(CR_2)_pA$, wherein R for each occurrence is independently alkyl, cycloalkyl, alkenyl, alkynyl, aryl, heterocycloalkyl, or heteroaryl; or two instance of R taken together form a 5-6 membered heterocycloalkyl; p for each occurrence is independently a whole number selected from 0-20; and A is $—CO_2H$, $—C≡CH$, $—CNS$, $—N_3$, $—NH_2$, $—SH$, Cl, Br, I, or N-maleimide; or two instance of $R^1$ taken together form a 5-6 membered cycloalkyl, heterocycloalkyl, aryl, or heteroaryl; or two instance of $R^2$ taken together form a 5-6 membered cycloalkyl, heterocycloalkyl, aryl, or heteroaryl.

In certain embodiments, each of m and n are independently a whole number selected from 0 and 1.

In certain embodiments, each of $R^1$ and $R^2$ is independently hydrogen, halide, nitrile, nitro, OR, $N(R)_2$, $O(C=O)R$, $N(R)(C=O)R$, $(C=O)R$, $CO_2R$, CHO, $(C=O)NR(R)_2$, $N(R)(C=O)NR(R)_2$, $O(C=O)NR(R)_2$, $N(R)(C=O)OR$, $—SO_2R$, $—SO_2NR_2$, wherein R for each instance is independently hydrogen, alkyl, alkenyl, alkynyl, aryl, or heteroaryl.

The compounds described herein can optionally comprise functionality that allows for covalent conjugation of the compounds described herein to other molecules. In such instances, at least one of $R^1$ and $R^2$ can be $—(CR_2)_pA$. In certain embodiments, one instance of $R^1$ and $R^2$ is $—(CH_2)_pA$, wherein p is 0-6, 0-4, or 0-2; and A is $—CO_2H$, $—C≡CH$, $—CNS$, $—N_3$, $—NH_2$, $—SH$, Cl, Br, I, or N-maleimide.

The unique photophysical properties of the compounds described herein enable numerous applications, such as use in luminescent identification cards, a driver's licenses, passports, identity papers, banknotes, checks, documents, paper, stock certificates, packaging components, credit cards, bank cards, labels, seals, postage stamps, textiles, liquids, and biological samples.

The compounds described herein can be used as imaging agents in biological systems by covalent conjugation to a targeting agent that selectively binds to a specific organ, tissue, cell, cellular receptor, polynucleotide, lipid, polypeptide, carbohydrate, small molecule, etc. In certain embodiments, the compounds described herein are covalently conjugated to a targeting agent. The targeting agent can be an antibody, an antibody fragment (such as Fab, Fab', F(ab')$_2$, and Fv), single chain (ScFv)) a peptide, an aptamer, or a small molecule that is capable of selectively binding to a target of interest, such as a carbohydrate, polynucleotide, lipid, polypeptide, protein, small molecule, cellular receptor, etc. Covalent conjugation of the compounds described herein and the targeting agent can be accomplished using well known methods known by the skilled person.

In certain embodiments, the first compound has the Formula 1a:

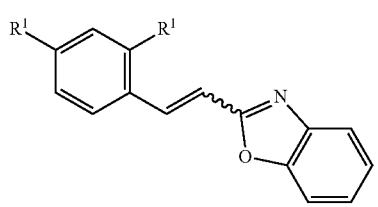

1a wherein $R^1$ for each instance is independently hydrogen, halide, nitrile, nitro, OR, $N(R)_2$, $O(C=O)R$, $N(R)(C=O)R$, $(C=O)R$, $CO_2R$, CHO, $(C=O)NR(R)_2$, $N(R)(C=O)NR(R)_2$, $O(C=O)NR(R)_2$, $N(R)(C=O)OR$, $—SO_2R$, —SO$_2$NR$_2$, alkyl, cycloalkyl, alkenyl, alkynyl, aryl, heterocycloalkyl, heteroaryl, or —(CR$_2$)$_p$A, wherein R for each occurrence is independently alkyl, cycloalkyl, alkenyl, alkynyl, aryl, heterocycloalkyl, or heteroaryl.

In certain embodiments, the first compound is selected from the group consisting of:

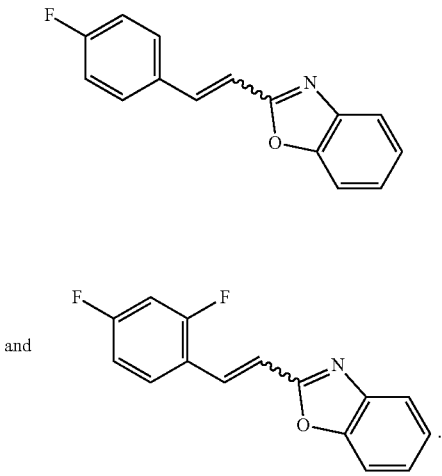

and

Irradiation of the first compound by UV light induces photodimerization thereby producing the second compound. In certain embodiments, the UV light has a wavelength between 300 nm to 400 nm; 350 nm to 400 nm; 350 nm to 380 nm; 360 nm to 380 nm; or 360 nm to 370 nm.

The second compound that is produced as a result of UV irradiation of the first compound can have the Formula 4a or 4b:

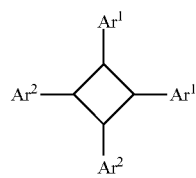

4a

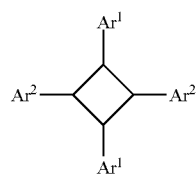

4b wherein Ar$^1$ and Ar$^2$ are as defined in any of the embodiments described herein.

Photodimerization of the first compound can result in the formation of one or more isomers of the second compound depending on the relative orientation of the substituents on the alkene during the [2+2] cycloaddition. All isomers (e.g., enantiomers, diastereomers, and regioisomers) are contemplated by the present disclosure.

In certain embodiments, the second compound can be one or more of the isomers selected from the group consisting of:

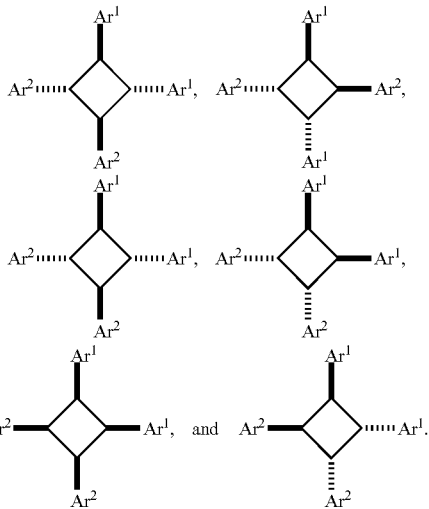

wherein m, n, R$^1$ and R$^2$ are as defined in any of the embodiments described herein.

In certain embodiments, the second compound is at least one compound selected from the group consisting of a compound of Formula 2a and a compound of Formula 2b:

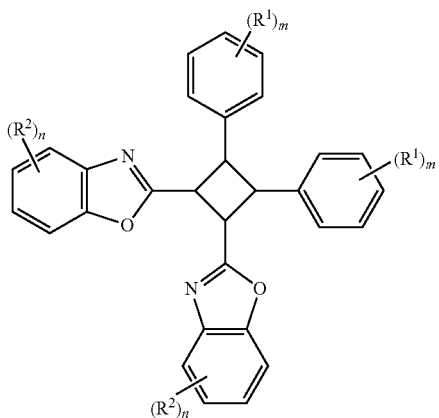

2a

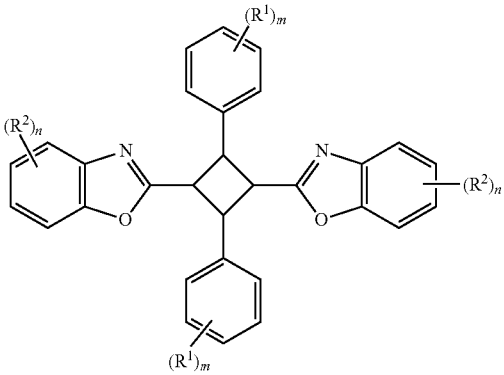

2b wherein m, n, R$^1$ and R$^2$ are as defined in any of the embodiments described herein.

In certain embodiments, the second compound is at least one compound selected from the group consisting of:

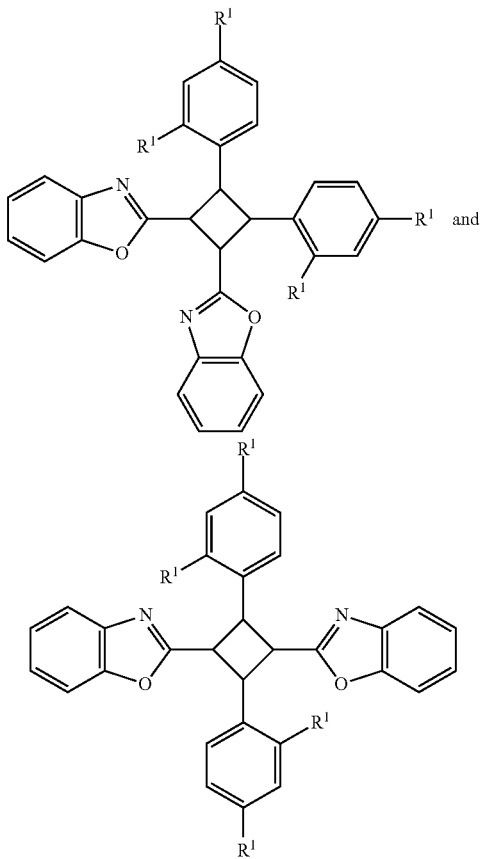 and wherein $R^1$ is as defined in any of the embodiments described herein.

The second compound may exhibit AIE at a wavelength between 350 to 650 nm depending on e.g., the structure of $Ar^1$ and $Ar^2$ and their isomerism. Without wishing to be bound by theory, it is believed that the AIE of the second compound is the result, at least in part, of through space intermolecular π-π interactions between $Ar^1$ and/or $Ar^2$ of two or more neighboring molecules of second compound. The energy levels of the π systems of $Ar^1$ and/or $Ar^2$ and the resulting AIE wavelength, can be adjusted by modification of the structure and/or stereochemistry of the $Ar^1$ and/or $Ar^2$ aryl or heteroaryl ring system(s) and the substituents covalently attached thereto. Such modifications are well within the skill or a person of ordinary skill in the art.

The second compound can undergo reverse [2+2] cycloaddition upon irradiation with UV light to yield the first compound. Thus, the multifunctional properties of the systems described herein can be controlled, e.g., turned on and off, as required, are reversible, and can be repeatedly used. In certain embodiments, the light used to irradiate the second compound for the reverse [2+2] cycloaddition in the range of 200 to 300 nm or 225 to 275 nm.

The present disclosure also provides a method for conversion of a first compound exhibiting aggregation-caused quenching (ACQ) to a second compound exhibiting aggregation-induced emission (AIE), the method comprising: providing a crystal comprising the first compound; and photoirradiating the first compound with ultraviolet light causing it to undergo photodimerization by [2+2] cycloaddition thereby forming the second compound, wherein photodimerization of the first compound optionally causes macroscopic actuation of the crystal, and wherein the first compound and the second compound are as defined in any embodiments described herein.

The present disclosure provides a photoresponsive actuator element which utilizes a first compound that can undergo a reversible dimerization [2+2] cycloaddition upon photoirradiation with UV and which can be repeatedly used as a non-contact-drive type actuator not requiring wiring or the like. Since the sensor and drive units of the photoresponsive actuator element of the present disclosure are integrated at the molecular level, size reduction to or below the micrometer order is possible. Moreover, the photoresponsive actuator element has the advantage of a fast response speed. Still another advantage of the photoresponsive actuator element of the present disclosure is that its displacement is determined by the light quantity (displacement can be controlled by controlling the light quantity). Advantageously, the photoresponsive actuator element may exhibit AIE properties.

In certain embodiments, the photoresponsive actuation system comprises a UV light source; and a photoresponsive actuator element comprising a crystal, wherein the crystal comprises a first compound, wherein photoirradiating the first compound with ultraviolet light from the UV light source causes the first compound to undergo photodimerization by [2+2] cycloaddition thereby forming a second compound, wherein photodimerization of the first compound causes actuation of the photoresponsive actuator element, and wherein the first compound and the second compound are as defined in any embodiments described herein.

Figure 21:
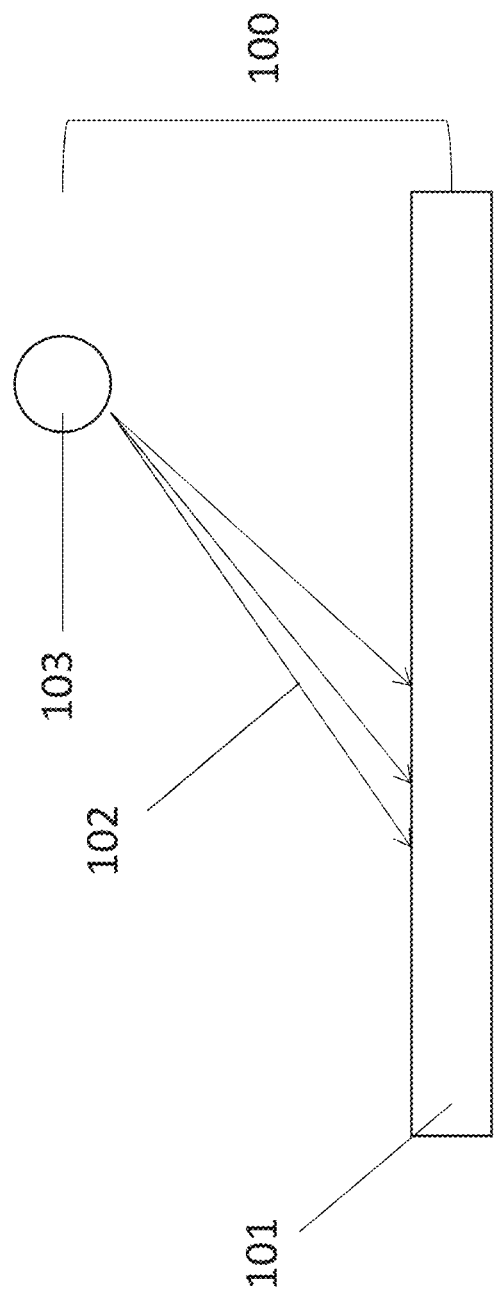
FIG. 21 shows an exemplary photoresponsive actuation system according to certain embodiments described herein.

An exemplary photoresponsive actuation system 100 is depicted in FIG. 21, which shows the photoresponsive actuator element 101, the UV light source 103, and UV light 102.

The photoresponsive actuation system described herein can comprise a UV light source. Any appropriate UV light source can be used including broadband and narrow band UV light sources. The UV light source can be any UV light emitting apparatus known in the art. In certain embodiments, the UV light source is a lamp, laser, or a light-emitting diode ("LED"). In some embodiments, the UV light source may emit light of one or more wavelengths selected between 300 nm to 400 nm chosen to excite the first compound. In certain embodiments, the UV light source emits light at a wavelength between 350 nm to 400 nm; 350 nm to 380 nm; 360 nm to 380 nm; or 360 nm to 370 nm. In certain embodiments, the UV light source may also emit one or more wavelengths selected between 200 to 300 nm chosen to excite the second compound and induce a retro [2+2] cycloaddition thereby generating the first compound. In certain embodiments, the UV light source emits light at a wavelength between 220 nm to 380 nm; 240 nm to 260 nm; or 250 nm to 260 nm.

The photoresponsive actuator element can take the form of any shape. In certain embodiments, the photoresponsive actuator element is present in a filament or a thin film. In certain embodiments, the thin film covers a substrate. The substrate can be any material.

The photoresponsive actuator element of the present disclosure can be driven in air, ordinarily at room temperature. The compounds used in the present disclosure have high thermal stability, as such, offer excellent practical properties from the viewpoint of application to an actuator product.

The photoresponsive actuator element of the present disclosure composed of the first compound can be used as an optically driven actuator in the field of micromechanics, for example.

Methods for operating the photoresponsive actuator system, the method comprising: providing the photoresponsive actuator element; and photoirradiating the first compound with ultraviolet light from the UV light source thereby causing actuation of the photoresponsive actuator element. In certain embodiments, the photoresponsive actuator element exhibits AIE properties.

Having described the invention, the following examples are given to illustrate specific applications of the invention including the best mode now known to perform the invention. These specific examples are not intended to limit the scope of the invention described in this application.

EXAMPLES

Characterizations: $^1$H and $^{13}$C NMR spectra were recorded on a Bruker ARX 400 NMR spectrometer using DMSO and tetramethyl silane (TMS; δ=0 ppm) as internal reference. UV/VIS absorption spectra were recorded on Shimadzu 2550 UV/VIS spectrophotometer. The photoluminescence (PL) spectra were recorded on a Horiba Fluorolog-3 spectrofluorometer. The absolute fluorescence quantum yield was measured by a calibrated integrating sphere (Labsphere). High-resolution mass spectroscopy (HRMS) was carried out on a GCT premier CAB048 mass spectrophotometer operating in MALDI-TOF mode. Single-crystal data was collected on a Bruker Smart APEXII charge-coupled device (CCD) diffractometer using graphite monochromated Cu Kα radiation (λ=1.54178 Å). The structures were solved by the direct methods and refined on F2 by full-matrix least-square using the SHELXTL-97 program. X-ray diffraction (XRD) pattern was collected on an X'per Pro (PANalytical) instrument with Cu Kα radiation (α=1.5418 Å) at 25° C. (scan range: 5-30°). The samples for XRD measurements were prepared by casting the solution on silica wafer and freeze-dried. The flashlight (365 nm, 3 W) was used as UV light source in photo cycloaddition studies Example 1—Synthesis of t-FPCBO transoid-2,2'-(2,4-bis(4-fluorophenyl)cyclobutene-1,3-diyl)bis(benzo[d]oxazole) (t-FPCBO)

t-FSBO powder (300 mg, 1.25 mmol) was added into grinding bowl and irradiated under the 365 nm UV light (20 mw/cm$^3$) with grinding and stirring for 20 min at the room temperature until the fluorescence become blue. The crude product was purified by column chromatography (silica gel) using ethyl acetate/hexane (v/v=1/10) as the eluent. White solid of t-FPCBO (0.20 g, 67%) was obtained in a yield of 67%. M.P. 192.0-193.0° C. $^1$H NMR (400 MHz, DMSO-d$_6$, 298 K) δ: 7.68-7.61 (m, 2H), 7.57-7.50 (m, 2H), 7.47 (dd, J=8.5, 5.5 Hz, 4H), 7.28 (dd, J=5.9, 3.2 Hz, 4H), 7.00 (t, J=8.8 Hz, 4H), 5.08-4.98 (m, 2H), 4.89 (dd, J=9.9, 7.1 Hz, 2H). $^{13}$C NMR (101 MHz, DMSO-d$_6$, 298 K) δ: 164.83 (s), 163.06 (s), 160.61 (s), 150.90 (s), 140.80 (s), 133.53 (d, J=3.2 Hz), 128.89 (d, J=8.1 Hz), 124.83 (s), 124.23 (s), 119.74 (s), 115.43 (s), 115.22 (s), 110.28 (s), 43.63 (s), 42.17 (s). FIRMS (MALDI-TOF), m/z: [M+H] calcd for C$_{30}$H$_{21}$F$_2$N$_2$O$_2$, 479.1493, found 479.1543.

Example 2—Synthesis of t-2FPCBO transoid-2,2'-(2,4-bis(2,4-fluorophenyl)cyclobutene-1,3-diyl)bis(benzo[d]oxazole) (t-2FPCBO) and cisoid-2,2'-(3,4-bis(2,4-fluorophenyl)cyclobutene-1,2-diyl)bis(benzo[d]oxazole) (c-2FPCBO)

t-2FSBO powder (300 mg, 1.16 mmol) was added into grinding bowl and irradiated under the 365 nm UV light (20 mw/cm$^3$) with grinding and stirring for 20 min at the room temperature until the fluorescence become blue. The crude product was purified by column chromatography (silica gel) using ethyl acetate/hexane (v/v=1/10) as the eluent. White solid of t-2FPCBO (20 mg) and white solid of c-2FPCBO were obtained in a total yield of 73%.

t-2FPCBO: M.P. 202.0-203.0° C. $^1$H NMR (400 MHz, DMSO-d$_6$, 298 K) δ: 7.74-7.59 (m, 4H), 7.59-7.49 (m, 2H), 7.33-7.27 (m, 3H), 7.19-7.08 (m, 2H), 6.93 (t, J=8.6 Hz, 2H), 5.20-5.10 (m, 2H), 5.07-4.98 (m, 2H). $^{13}$C NMR (101 MHz, DMSO-d$_6$, 298 K) δ: 165.09 (d, J=14.8 Hz), 150.88 (s), 140.80 (s), 125.61 (s), 124.87 (s), 121.58 (s), 120.02 (s), 118.32 (s), 110.84 (s), 39.06 (s), 38.11 (s). HRMS (MALDI-TOF), m/z: [M-F-H] calcd for C$_{30}$H$_{18}$F$_3$N$_2$O$_2$, 495.1399, found 495.1350.

c-2FPCBO: M.P. 206.0-207.0° C. $^1$H NMR (400 MHz, DMSO-d$_6$, 298 K) δ: 7.66-7.54 (m, 4H), 7.50-7.41 (m, 2H), 7.30-7.22 (m, 4H), 7.09 (dd, J=13.6, 6.0 Hz, 2H), 6.99 (td, J=8.5, 2.5 Hz, 2H), 5.10 (d, J=10.6 Hz, 4H). $^{13}$C NMR (101 MHz, DMSO-d$_6$, 298 K) δ: 165.59 (s), 150.87 (s), 140.83 (s), 134.78 (d, J=2.9 Hz), 129.95 (d, J=8.0 Hz), 125.35 (s), 124.73 (s), 119.87 (s), 115.44 (s), 115.23 (s), 110.89 (s), 43.26 (s), 41.66 (s). HRMS (MALDI-TOF), m/z: [M-F-H] calcd for C$_{30}$H$_{18}$F$_3$N$_2$O$_2$, 495.1399, found 495.1298.

What is claimed:

1. A method for conversion of a first compound exhibiting aggregation-caused quenching (ACQ) to a second compound exhibiting aggregation-induced emission (AIE), the method comprising:

providing a crystal comprising the first compound, wherein the first compound is:

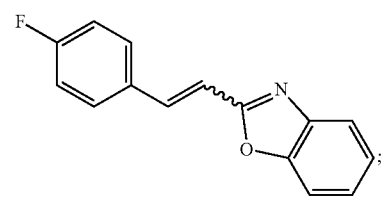 [SMILES: Fc1ccc(C=Cc2nc3ccccc3o2)cc1]

and photoirradiating the first compound with ultraviolet (UV) light causing it to undergo photodimerization by [2+2] cycloaddition thereby forming the second compound, wherein the second compound is:

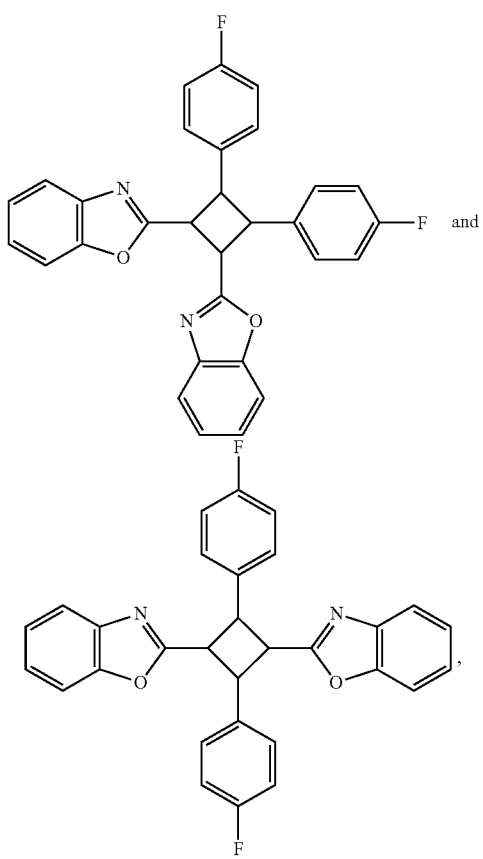

wherein photodimerization of the first compound optionally causes macroscopic actuation of the crystal.

2. A photoresponsive actuation system, the system comprising:
   a UV light source; and
   a photoresponsive actuator element comprising a crystal, wherein the crystal comprises a first compound, wherein the first compound is:

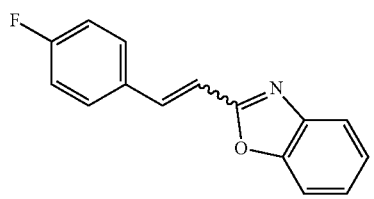 [SMILES: Fc1ccc(C=Cc2nc3ccccc3o2)cc1]

or a conjugate salt thereof, wherein photoirradiating the first compound with UV light from the UV light source causes the first compound to undergo photodimerization by [2+2] cycloaddition thereby forming a second compound, wherein the second compound is at least one compound selected from the group consisting of:

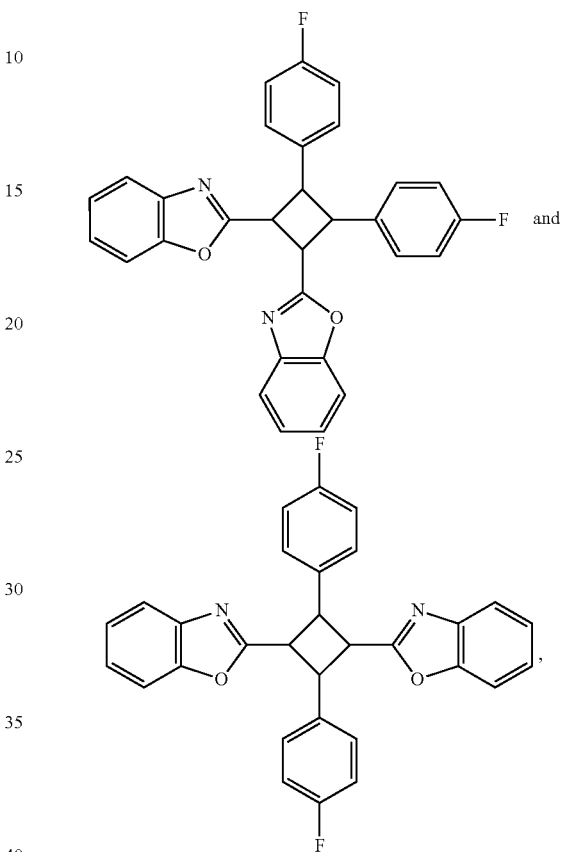

wherein photodimerization of the first compound causes actuation of the photoresponsive actuator element.

3. The system of claim 2, wherein the photoresponsive actuator element is present as a thin layer on the surface of a substrate.

4. A method for operating the photoresponsive actuator system of claim 2, the method comprising:
   providing the photoresponsive actuator element; and
   photoirradiating the first compound with ultraviolet light from the UV light source thereby causing actuation of the photoresponsive actuator element.

* * * * *